(12) United States Patent
Eguchi

(10) Patent No.: US 12,023,186 B2
(45) Date of Patent: Jul. 2, 2024

(54) MOBILE RADIOGRAPHY APPARATUS

(71) Applicant: FUJIFILM CORPORATION, Tokyo (JP)

(72) Inventor: Koichi Eguchi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 261 days.

(21) Appl. No.: 17/718,274

(22) Filed: Apr. 11, 2022

(65) Prior Publication Data

US 2022/0233157 A1 Jul. 28, 2022

Related U.S. Application Data

(63) Continuation of application No. PCT/JP2020/039423, filed on Oct. 20, 2020.

(30) Foreign Application Priority Data

Oct. 31, 2019 (JP) .................................. 2019-199331

(51) Int. Cl.
 *A61B 6/00* (2006.01)
(52) U.S. Cl.
 CPC .......... *A61B 6/4405* (2013.01); *A61B 6/4441* (2013.01); *A61B 6/54* (2013.01)
(58) Field of Classification Search
 CPC ....... A61B 6/469; A61B 6/505; A61B 6/5217; G06T 2207/10116; G06T 2207/20081;
 (Continued)

(56) References Cited

U.S. PATENT DOCUMENTS

| 5,503,416 A | 4/1996 | Aoki et al. |
| 2011/0096910 A1* | 4/2011 | Yao ...................... A61B 6/4405 |
| | | 378/197 |

FOREIGN PATENT DOCUMENTS

| EP | 3391822 A1 | 10/2018 |
| JP | H01-232936 A | 9/1989 |
| | (Continued) | |

OTHER PUBLICATIONS

International Search Report issued in International Application No. PCT/JP2020/039423 dated Dec. 8, 2020.
(Continued)

*Primary Examiner* — Dani Fox
(74) *Attorney, Agent, or Firm* — SOLARIS Intellectual Property Group, PLLC

(57) ABSTRACT

A radiography apparatus includes: an irradiator that emits radiation; a carriage portion on which the irradiator is mounted and which is capable of traveling; steering casters which are provided in the carriage portion and are connected to a steering and whose steering angle is given by an operation of the steering; free casters which are provided in the carriage portion and are not connected to the steering and whose steering angle is changed subordinately according to a direction of force applied to the carriage portion; and a switching mechanism that selectively switches between a first grounded state in which the free casters are separated from a floor and the steering casters are grounded to the floor and a second grounded state in which the free casters are grounded to the floor and the steering casters are separated from the floor.

9 Claims, 17 Drawing Sheets

(58) Field of Classification Search
CPC . G06T 2207/20084; G06T 2207/30008; G06T 7/0014; G06T 7/12; G06T 7/194
See application file for complete search history.

(56) References Cited

FOREIGN PATENT DOCUMENTS

| | | |
|---|---|---|
| JP | H04-39168 U1 | 4/1992 |
| JP | H08-336514 A | 12/1996 |
| JP | 2005-224516 A | 8/2005 |
| JP | 2011-87923 A | 5/2011 |
| WO | 2018060511 A2 | 4/2018 |

OTHER PUBLICATIONS

Written Opinion of the ISA issued in International Application No. PCT/JP2020/039423 dated Dec. 8, 2020.
Extended European Search Report dated Nov. 21, 2022, issued in corresponding EP Patent Application No. 20882558.8.
English language translation of the following: Office action dated Nov. 22, 2022 from the JPO in a Japanese patent application No. 2021-553465 corresponding to the instant patent application.

* cited by examiner

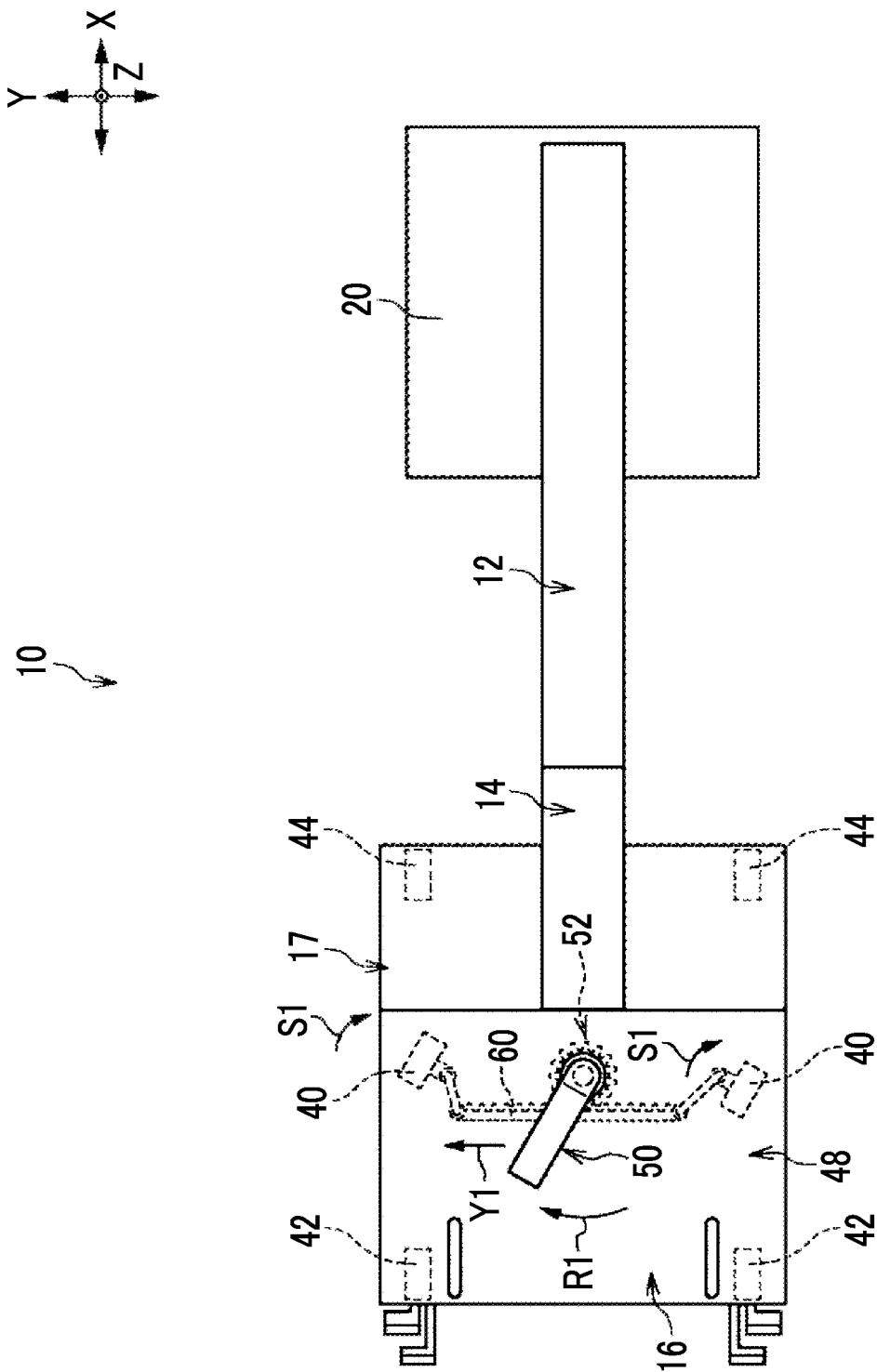

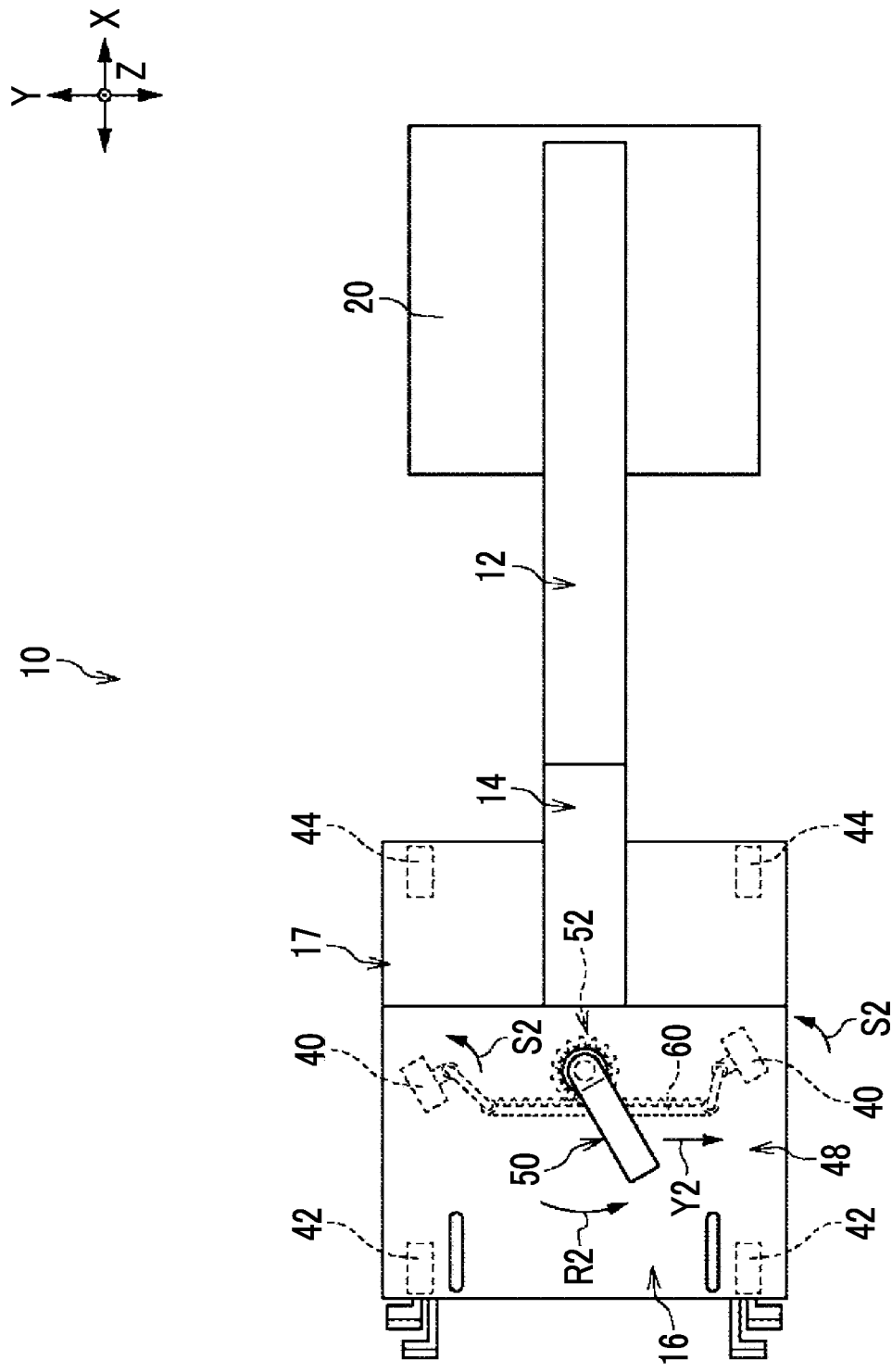

MOBILE RADIOGRAPHY APPARATUS

CROSS-REFERENCE TO RELATED APPLICATIONS

This application is a continuation application of International Application No. PCT/JP2020/039423, filed Oct. 20, 2020, the disclosure of which is incorporated herein by reference in its entirety. Further, this application claims priority from Japanese Patent Application No. 2019-199331, filed on Oct. 31, 2019, the disclosure of which is incorporated herein by reference in its entirety.

BACKGROUND

1. Technical Field

The present disclosure relates to a mobile radiography apparatus.

2. Description of the Related Art

A mobile radiography apparatus including an irradiation unit that emits radiation and a carriage portion that can travel is known (see JP2011-87923A). The carriage portion is provided with a plurality of casters, and a support portion that supports an arm provided with the irradiation unit and a main body portion are mounted on the carriage portion.

Two types of casters of steering casters (main wheels) and free casters (auxiliary wheels) are provided in the carriage portion of the mobile radiography apparatus (X-ray imaging apparatus) disclosed in JP2011-87923A. The steering caster is a caster to which a steering is connected, and a steering angle is given to the steering caster by the operation of the steering. Therefore, the traveling direction of the carriage portion can be fixed by the operation of the steering. The free caster is not connected to the steering, and a steering angle thereof is changed subordinately according to force applied to the carriage portion.

SUMMARY

In some cases, this mobile radiography apparatus is used in a hospital room and an operating room as well as in an imaging room. In a case in which a patient who has difficulty in moving to the imaging room is imaged, the mobile radiography apparatus is carried into the patient's hospital room and used in the hospital room. In addition, in a case in which a moving image of a treatment target part of a patient undergoing surgery is captured, the mobile radiography apparatus is carried into the operating room and used in the operating room. In a case in which the use of the mobile radiography apparatus in a plurality of usage situations is considered, operability required for the carriage portion changes depending on each usage situation.

For example, since the hospital room is smaller than the imaging room, in the hospital room, turning in a smaller radius is more required than in the imaging room. In addition, in a case in which the mobile radiography apparatus is used in a narrow hospital room with many obstacles including a bed, there is a demand for easily changing the direction of the carriage portion by pushing and pulling the mobile radiography apparatus in various directions without bothering to operate the steering. On the other hand, in some cases, for example, imaging is performed while sequentially moving an imaging position along the body axis of the patient during surgery. In this situation, in a case in which the carriage portion sways, it is difficult to perform appropriate imaging. Therefore, there is a demand for fixing the position of the steering to fix the traveling direction of the carriage portion.

In the mobile radiography apparatus disclosed in JP2011-87923A, since the steering casters are always grounded, the traveling direction of the carriage portion is fixed by the position of the steering. Therefore, since it is difficult to change the direction of the carriage portion without operating the steering, the carriage portion is not turned in a small radius, and the mobile radiography apparatus is not easy to use in a case in which it is used in a narrow hospital room. On the other hand, in a case in which the carriage portion having only the free casters without the steering casters is used, the carriage portion is turned in a small radius. However, in a case in which an operator wants to fix the traveling direction of the carriage portion, the mobile radiography apparatus is not easy to use. As described above, the operability required for the carriage portion changes according to the usage situation.

The technology according to the present disclosure provides a mobile radiography apparatus that can change the operability of a carriage portion according to a usage situation.

According to a first aspect of the present disclosure, there is provided a mobile radiography apparatus comprising: an irradiation unit that emits radiation; a carriage portion on which the irradiation unit is mounted and which is capable of traveling; steering casters which are provided in the carriage portion and are connected to a steering and whose steering angle is given by an operation of the steering; free casters which are provided in the carriage portion and are not connected to the steering and whose steering angle is changed subordinately according to a direction of force applied to the carriage portion; and a switching mechanism that selectively switches between a first grounded state in which the free casters are separated from a floor and the steering casters are grounded to the floor and a second grounded state in which the free casters are grounded to the floor and the steering casters are separated from the floor.

According to the above configuration, the switching mechanism selectively switches the grounded state of the free casters and the steering casters to change the operability of the carriage portion according to the usage situation.

That is, for the operability of the carriage portion, the free casters are grounded such that the carriage portion can be turned in a small radius. The steering casters are grounded to fix the traveling direction of the carriage portion. The turning of the carriage portion in a small radius improves usability in a case in which the mobile radiography apparatus is used in a small hospital room. The fixation of the traveling direction improves usability in a case in which continuous imaging is performed while moving an imaging position.

According to a second aspect of the present disclosure, in the mobile radiography apparatus according to the first aspect, the switching mechanism may raise and lower the free casters with respect to the steering casters to switch between the first grounded state and the second grounded state.

In general, the steering casters are heavier than the free casters since they are connected to the steering. Here, according to the above configuration, the switching mechanism raises and lowers the free casters, which makes it possible to easily switch the grounded state of the casters with a small force as compared to a configuration in which the steering casters are raised and lowered.

According to a third aspect of the present disclosure, in the mobile radiography apparatus according to the second aspect, the switching mechanism may have a pedal that raises and lowers the free casters.

According to the above configuration, the free casters can be raised and lowered by stepping on the pedal. Therefore, it is possible to switch the grounded state of the casters while manually operating the mobile radiography apparatus.

According to a fourth aspect of the present disclosure, in the mobile radiography apparatus according to any one of the first to third aspects, always-grounded casters that are grounded to the floor in both the first grounded state and the second grounded state may be provided, in addition to the free casters and the steering casters.

According to the above configuration, the always-grounded casters are provided in addition to the free casters and the steering casters. Therefore, it is possible to stably move the carriage portion even in a case in which one of the free casters and the steering casters is separated from the floor. In addition, in a case in which the grounded state of the free casters and the steering casters is switched, the postural instability of the carriage portion is also suppressed.

According to a fifth aspect of the present disclosure, in the mobile radiography apparatus according to the fourth aspect, an arm that supports the irradiation unit and a main body portion including a control unit that controls the irradiation unit may be mounted on the carriage portion, and the always-grounded casters may be casters whose steering angle is changed subordinately similarly to the free casters. In a case in which a side on which the arm is provided is a front side of the carriage portion and a side on which the main body portion is provided is a rear side of the carriage portion, the always-grounded casters, the steering casters, and the free casters may be disposed in this order from the front side to the rear side of the carriage portion.

According to the above configuration, the steering casters are disposed between the always-grounded casters and the free casters in the front-rear direction of the main body portion. Therefore, the steering casters can be disposed at a position close to the position of the center of gravity of the main body portion. As a result, it is possible to suppress the postural instability of the main body from in a case in which the steering is operated.

According to a sixth aspect of the present disclosure, in the mobile radiography apparatus according to the fifth aspect, the steering casters may be disposed at a position of a center of gravity in a front-rear direction of the carriage portion.

According to the above configuration, since the steering casters are disposed at the position of the center of gravity in the entire mobile radiography apparatus, it is possible to further suppress the postural instability of the main body portion in a case in which the steering is operated.

According to a seventh aspect of the present disclosure, in the mobile radiography apparatus according to the fifth or sixth aspect, the arm may have two end portions. The irradiation unit may be provided at one end of the arm, and an image receiving unit that receives the radiation, which has been emitted from the irradiation unit and transmitted through the subject, may be provided at the other end of the arm.

According to the above configuration, the irradiation unit and the image receiving unit can be integrally held by the arm. Therefore, for example, it is possible to perform imaging while moving the carriage portion in the body axis direction of the subject during surgery.

According to an eighth aspect of the present disclosure, the mobile radiography apparatus according to any one of the first to seventh aspects may further comprise a steering lock mechanism that locks an operation by the steering in the second grounded state in which the steering casters are separated from the floor.

According to the above configuration, the steering lock mechanism that locks the operation by the steering in a case in which the steering casters are separated from the floor is provided. Therefore, it is possible to the postural instability of the mobile radiography apparatus caused by the movement of the steering casters in a case in which the main body portion is moved by the free casters.

According to a ninth aspect of the present disclosure, in the mobile radiography apparatus according to any one of the first to eighth aspects, a handle for pushing and pulling the carriage portion may be provided separately from the steering.

According to the above configuration, since the handle for pushing and pulling the carriage portion separately from the steering is provided, it is easy to operate the mobile radiography apparatus in a case in which the carriage portion is moved by the free casters.

According to the technology of the present disclosure, it is possible to change the operability of the carriage portion according to the usage situation.

BRIEF DESCRIPTION OF THE DRAWINGS

Exemplary embodiments according to the technique of the present disclosure will be described in detail based on the following figures, wherein:

FIG. 7A is a plan view illustrating a state in which a steering of the mobile radiography apparatus illustrated in FIG. 6 is operated in one direction, FIG. 7B is a plan view illustrating a state in which the steering of the mobile radiography apparatus illustrated in FIG. 6 is operated in the other direction.

DETAILED DESCRIPTION

Figure 1:
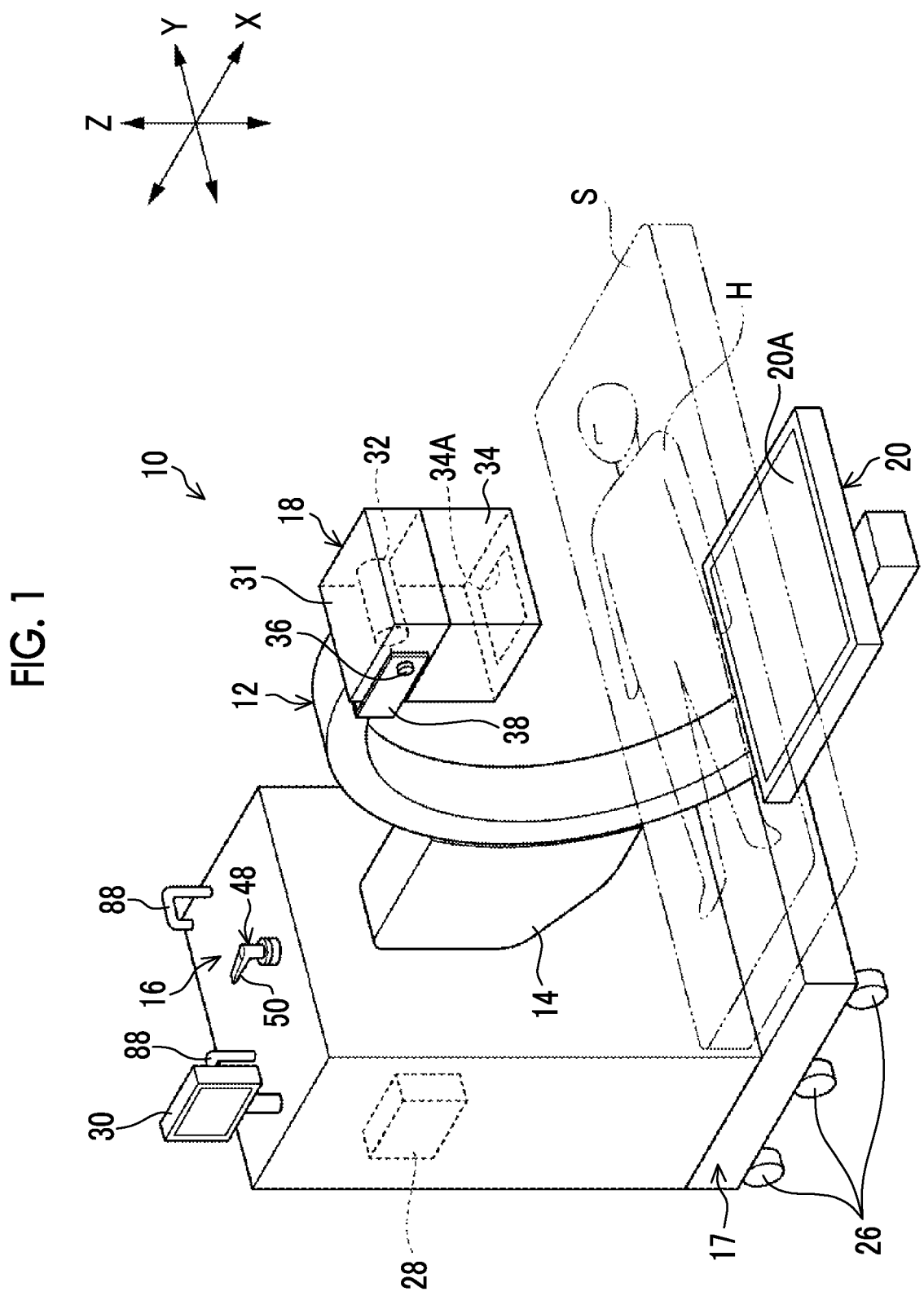
FIG. 1 is an overall perspective view illustrating a mobile radiography apparatus according to an example of an embodiment.

Hereinafter, a mobile radiography apparatus according to an example of an embodiment of the present disclosure will be described with reference to the drawings. In addition, in the drawings, an arrow X indicates a front-rear direction of the mobile radiography apparatus, an arrow Y indicates a width direction of the mobile radiography apparatus, and an arrow Z indicates a vertical direction.

(Overall Configuration of Mobile Radiography Apparatus)

A mobile radiography apparatus 10 according to this embodiment illustrated in FIG. 1 is an apparatus that captures a radiographic image of a subject H. The mobile radiography apparatus 10 can capture, for example, moving images and still images of the subject H. The capture of the moving image is performed, for example, in a case in which a treatment target part of the subject H is displayed as a moving image during surgery (also referred to as fluoroscopy or the like). In the capture of the moving image, for example, the moving image of the subject H is displayed on a monitor (not illustrated) that is provided separately from the mobile radiography apparatus 10. Of course, data of the captured moving image may be stored in a memory of the mobile radiography apparatus 10. In addition, in the case of the capture of the still image, the captured still image may be displayed on the monitor or may be stored in the memory of the mobile radiography apparatus 10.

As illustrated in FIG. 1, the mobile radiography apparatus 10 includes an arm 12 (referred to as a C-arm or the like) having a C-shape (an arc shape) in a side view and a main body portion 16 to which a support portion 14 is attached. The arm 12, the support portion 14, and the main body portion 16 are mounted on a carriage portion 17. In addition, hereinafter, it is assumed that the side of the mobile radiography apparatus 10 on which the arm 12 is provided is the front side of the mobile radiography apparatus 10 and the side on which the main body portion 16 is provided is the rear side of the mobile radiography apparatus 10.

(Configuration of Arm)

The arm 12 has two end portions. An irradiation unit 18 is provided at one end of the arm 12, and an image receiving unit 20 is provided at the other end. The arm 12 can hold the irradiation unit 18 and the image receiving unit 20 in a posture in which they face each other. A space, into which the subject H and a bed S on which the subject H lies supine can be inserted, is ensured between the irradiation unit 18 and the image receiving unit 20. Further, in the following description, in some cases, in a side view of the arm 12 (as viewed from the Y direction in FIG. 1), a direction in which the irradiation unit 18 and the image receiving unit 20 are provided is referred to as the front side of the arm 12, and a side close to the support portion 14 is referred to as the rear side of the arm 12. The irradiation unit 18 is an example of an irradiator according to the present disclosure. The image receiving unit 20 is an example of an image receiver according to the present disclosure.

Figure 2A:
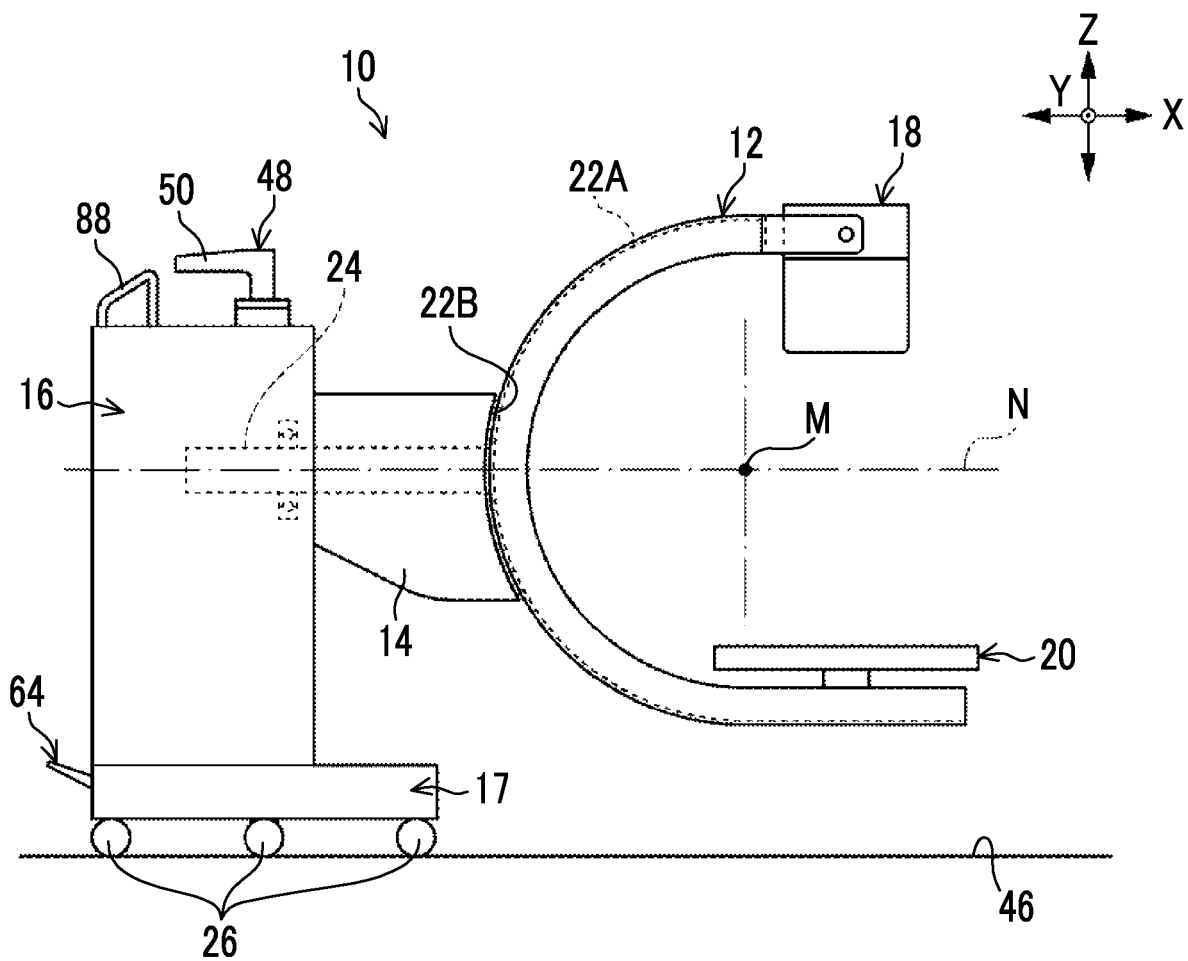
FIG. 2A is a side view illustrating the mobile radiography apparatus according to an example of the embodiment.

As illustrated in FIG. 2A, the arm 12 is orbitally rotatable about an axis line M (an axis line parallel to the Y axis) with respect to a track portion 22B that is provided in the support portion 14. Further, the arm 12 is axially rotatable about an axis line N (an axis line parallel to the X axis) with respect to a bearing portion 23 that is provided in the main body portion 16.

Specifically, the track portion 22B has an arc shape that has the same radius as the arc of the arm 12. Moreover, a fitting portion 22A that is fitted to the track portion 22B is provided in an outer peripheral portion of the arm 12. The fitting portion 22A has an arc shape following the shape of the arm 12. The track portion 22B has, for example, a groove shape, and the fitting portion 22A having a protruding shape is fitted to the track portion 22B.

As illustrated in FIG. 2A, the fitting portion 22A formed in the arm 12 slides along the track portion 22B formed on the support portion 14. Therefore, the arm 12 can be orbitally rotated about the axis line M at the center of the arc of the arm 12 as a rotation center with respect to the support portion 14 and the main body portion 16.

Figure 2B:
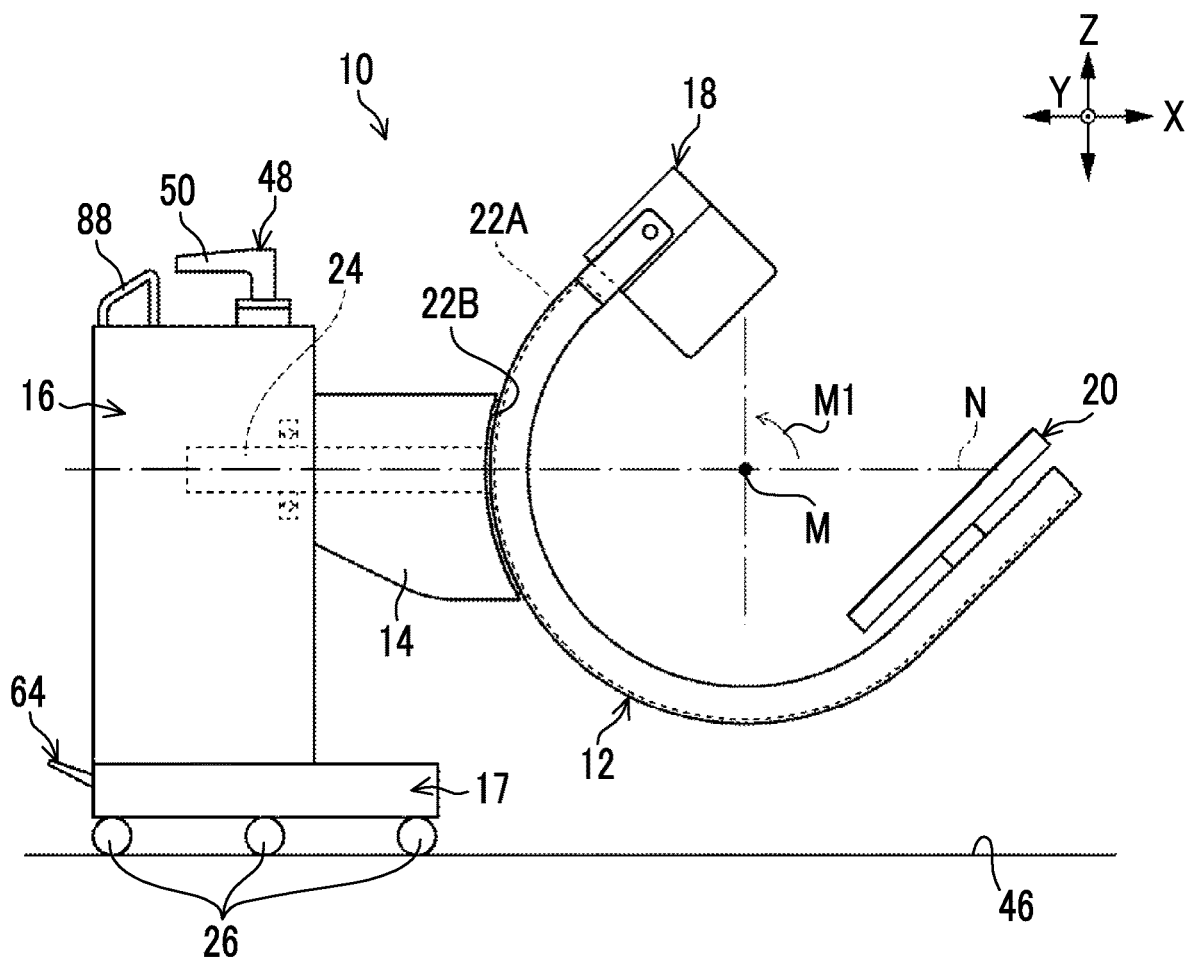
FIG. 2B is a side view illustrating a state in which an arm of the mobile radiography apparatus illustrated in FIG. 2A is rotated in a direction of an arrow M1.
Figure 2C:
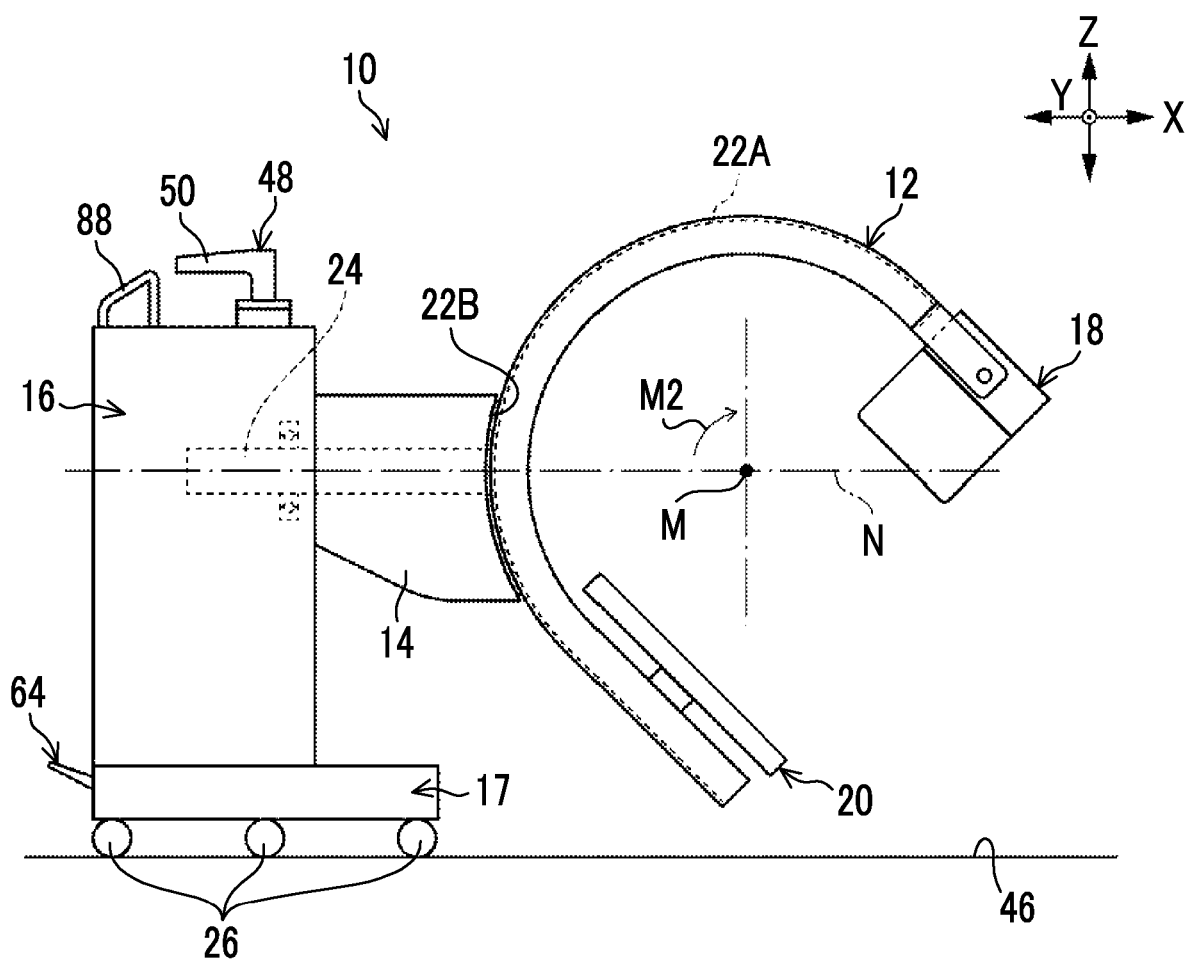
FIG. 2C is a side view illustrating a state in which the arm of the mobile radiography apparatus illustrated in FIG. 2A is rotated in a direction of an arrow M2.

That is, as illustrated in FIGS. 2B and 2C, it is possible to orbitally rotate the arm 12 about the axis line M in the direction of an arrow M1 (counterclockwise in FIG. 2B) and the direction of an arrow M2 (clockwise in FIG. 2C). Therefore, the irradiation unit 18 and the image receiving unit 20 provided at both ends of the arm 12 can be rotated about the body axis (an axis parallel to the Y axis) of the subject H (see FIG. 1) in a posture in which they face each other.

Further, as illustrated in FIG. 2A, one end of a support shaft 24 that extends in the front-rear direction (X direction) of the mobile radiography apparatus 10 is fixed to the arm 12. The other end of the support shaft 24 is supported by the main body portion 16 through the bearing portion 23. The support shaft 24 is rotated about the axis line N with respect to the bearing portion 23 such that the arm 12 and the support portion 14 are rotatable about the axis line N of the support shaft 24 as a rotation center with respect to the main body portion 16 as illustrated in FIGS. 3A to 3C.

Figure 3A:
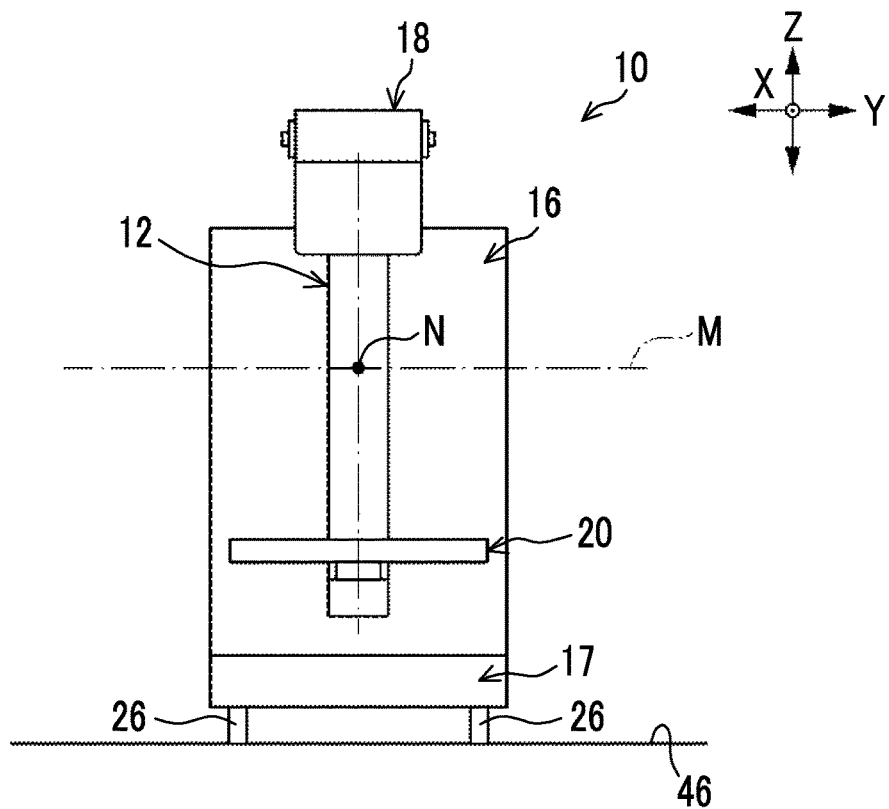
FIG. 3A is a front view illustrating the mobile radiography apparatus according to an example of the embodiment.
Figure 3B:
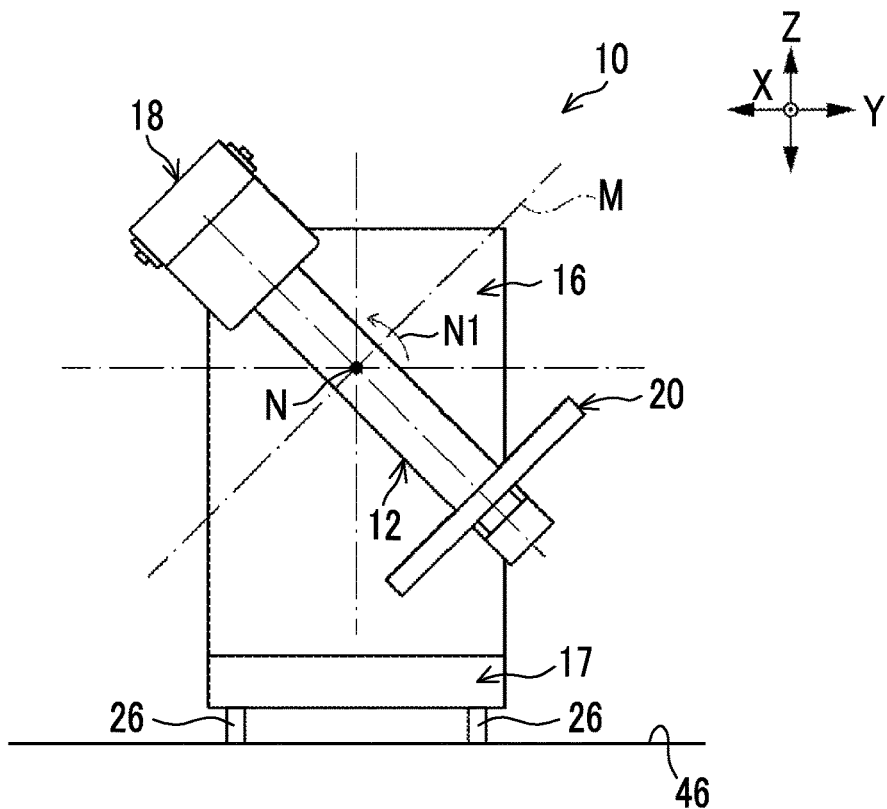
FIG. 3B is a front view illustrating a state in which the arm of the mobile radiography apparatus illustrated in FIG. 3A is rotated in a direction of an arrow N1.
Figure 3C:
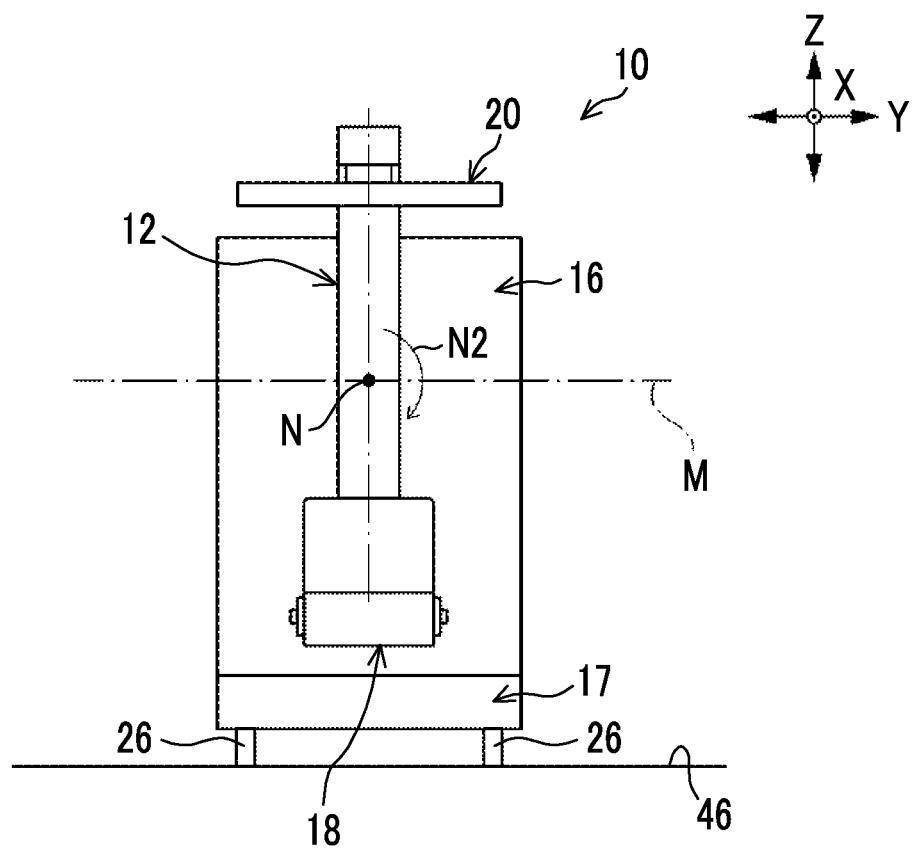
FIG. 3C is a front view illustrating a state in which the arm of the mobile radiography apparatus illustrated in FIG. 3A is rotated 180° in a direction of an arrow N2.

That is, as illustrated in FIGS. 3B and 3C, it is possible to rotate the arm 12 about the axis line N in the direction of an arrow N1 (counterclockwise in FIG. 3B) and the direction of an arrow N2 (clockwise in FIG. 3C). Therefore, it is possible to reverse the positions of the irradiation unit 18 and the image receiving unit 20 provided at both ends of the arm 12 with respect to the subject H (see FIG. 1) in the vertical direction (Z-axis direction).

Here, in the posture of the arm 12 in which the irradiation unit 18 is disposed above the image receiving unit 20 as illustrated in FIG. 3A, a radiation tube 32 (see FIG. 1) included in the irradiation unit 18 is located above the subject H. Therefore, this posture is called, for example, an overtube posture. In addition, in the posture of the arm 12 in which the irradiation unit 18 is disposed below the image receiving unit 20 illustrated in FIG. 3C, the radiation tube 32 is located below the subject H. Therefore, this posture is called, for example, an undertube posture.

In the overtube posture, it is possible to increase a distance between the irradiation unit 18 and the subject H (see FIG. 1), as compared to the undertube posture. This makes it possible to image a relatively wide region in the overtube posture. Therefore, the overtube posture is mainly used to capture the still image of the subject H. On the other hand, in the undertube posture, the radiation emitted from the irradiation unit 18 is partially blocked by, for example, the bed S. Therefore, in the undertube posture, it is possible to reduce the amount of radiation exposure to, for example, a radiology technician or an operator (not illustrated) around the subject H (see FIG. 1). Therefore, the undertube posture is used for the capture of the moving image of the subject H in which radiation is continuously emitted.

(Configuration of Main Body Portion)

As illustrated in FIG. 1, the main body portion 16 of the mobile radiography apparatus 10 includes a control unit 28 that controls each unit, such as the irradiation unit 18, in the mobile radiography apparatus 10 and an operation panel 30 of, for example, a touch panel type. In addition, the main body portion 16 comprises various switches (not illustrated) including, for example, a power switch of the mobile radiography apparatus 10, a power circuit that supplies power to each unit of the mobile radiography apparatus 10, a battery, and the like.

The operation panel 30 functions as an operation unit that inputs an operation instruction to each unit of the mobile radiography apparatus 10 to operate each unit and a display unit that displays various kinds of information, such as a warning message and a radiographic image output from the image receiving unit 20. The control unit 28 is an example of a controller according to the present disclosure.

(Configuration of Control Unit)

The control unit 28 transmits a control signal to the radiation tube 32 of the irradiation unit 18, which will be described below, to control, for example, the tube voltage, tube current, and irradiation time of radiation of the radiation tube 32. The control unit 28 controls the tube voltage to control the energy of the radiation. In addition, the control unit 28 controls the tube current and the irradiation time to control a radiation dose. In practice, since a high voltage is applied to the radiation tube 32, the control unit 28 controls the radiation tube 32 through a high-voltage generation device (not illustrated). In imaging, imaging conditions including, for example, the tube voltage, the tube current, and the irradiation time are set through the operation panel 30. The control unit 28 operates the irradiation unit 18 on the basis of the set imaging conditions.

The control unit 28 directs the irradiation unit 18 to perform moving image capture irradiation in which the irradiation unit 18 continuously emits radiation such that a moving image of the subject H can be captured. In a case in which a moving image is captured, the control unit 28 operates a detector of the image receiving unit 20 which will be described below in synchronization with the moving image capture irradiation by the irradiation unit 18. In a case in which a moving image is captured, basically, the irradiation time is not set as the imaging condition, and instructions to start and end the capture of the moving image are input through the operation panel 30. In a case in which the instruction to start the capture of a moving image is input, the control unit 28 directs the irradiation unit 18 to start the emission of radiation under preset imaging conditions.

In the capture of a moving image, the detector repeats an image detection operation at a preset frame rate while the moving image capture irradiation is performed. The image output by the detector is transmitted to the control unit 28. The control unit 28 sequentially outputs the received images to a monitor (not illustrated). Therefore, the moving image of the subject H is displayed on the monitor.

In addition, the control unit 28 directs the irradiation unit 18 to perform still image capture irradiation in which the irradiation unit 18 emits radiation for a shorter time than in the moving image capture irradiation such that a still image of the subject H can be captured.

In the capture of a still image, the control unit 28 operates the detector of the image receiving unit 20 in synchronization with the irradiation timing in the still image capture irradiation by the irradiation unit 18. For example, an instruction to capture a still image is input through an irradiation switch (not illustrated) that is connected to the control unit 28. In the capture of a still image, the irradiation time is, for example, in the order of several tens of milliseconds to several hundreds of milliseconds. In a case in which the instruction to capture a still image is input, the control unit 28 operates the irradiation unit 18 on the basis of preset imaging conditions. In the capture of a still image, in a case in which the set irradiation time elapses, the irradiation operation of the irradiation unit 18 ends since the irradiation time is set in the imaging conditions.

In a case in which the irradiation ends, the detector starts to output the detected image. The image output by the detector is transmitted to the control unit 28. The control unit 28 stores data of the still image in a memory (not illustrated). Then, the stored still image is displayed on the monitor (not illustrated). Therefore, the still image of the subject H is displayed on the monitor. Further, the still image may be displayed on the operation panel 30 in order to check the captured still image immediately after imaging.

(Configuration of Irradiation Unit)

The irradiation unit 18 comprises a radiation source 31 and an irradiation field limiter 34. The radiation source 31 comprises the radiation tube 32 that generates radiation. The radiation is, for example, X-rays. The radiation tube 32 generates radiation by colliding electrons generated from a cathode with a target (anode). The position where the electrons collide with the target is a focus where radiation is emitted.

In addition, the irradiation field limiter 34 is provided below the radiation source 31. The irradiation field limiter 34 (also referred to as a collimator or the like) has a rectangular irradiation opening 34A. The radiation generated by the radiation tube 32 is emitted to the subject H through the irradiation opening 34A. The irradiation field limiter 34 can adjust the opening area of the irradiation opening 34A. The irradiation field limiter 34 has, for example, four shielding plates (not illustrated) that shield radiation. In each of the four shielding plates, each side corresponds to each side of the irradiation opening 34A and defines the irradiation opening 34A. The position of the shielding plates is changed to adjust the opening area of the irradiation opening 34A, and the irradiation field of the radiation emitted from the irradiation unit 18 is changed.

Further, the irradiation unit 18 can be rotated about an axis line of a rotation shaft 36 that extends in the width direction (the Y direction in FIG. 1) of the mobile radiography apparatus 10 as a rotation center with respect to the arm 12. Specifically, a pair of attachment plates 38 (only one attachment plate is illustrated in FIG. 1) are fixed to one end of the arm 12.

The pair of attachment plates 38 are disposed such that both sides of the irradiation unit 18 in the width direction are interposed therebetween and are connected to both side surfaces of the irradiation unit 18 in the width direction. The rotation shafts 36 are provided on each of the side surfaces of the irradiation unit 18 facing the attachment plates 38 so as to protrude. The rotation shafts 36 are supported by the pair of attachment plates 38 through bearings (not illustrated). Therefore, the irradiation unit 18 can be rotated about the axis line of the rotation shaft 36 as the rotation center with respect to the attachment plates 38, and the orientation of the irradiation opening 34A of the irradiation unit 18 can be changed in the front-rear direction of the arm 12. The orientation of the irradiation opening 34A can be changed to change the irradiation direction of radiation.

Further, the irradiation unit 18 is connected to, for example, the control unit 28 and a power circuit (not illustrated) of the main body portion 16 by a cable (not illustrated) including a signal line for transmitting a control signal and a power line for supplying power.

(Configuration of Image Receiving Unit)

As illustrated in FIG. 1, the image receiving unit 20 is provided at the other end of the arm 12 which is a position facing the irradiation unit 18. Furthermore, in this embodiment, the image receiving unit 20 is fixed to the other end of the arm 12 so as not to be detachable. However, the image receiving unit 20 may be attached to the other end of the arm 12 so as to be detachable.

The image receiving unit 20 comprises the detector provided in a housing. The image receiving unit 20 has an image receiving surface 20A that receives the radiation which has been emitted from the irradiation unit 18 and then transmitted through the subject H. The radiation carrying the information of the subject H is incident on the image receiving surface 20A.

The detector is, for example, a flat panel detector (FPD) of a digital radiography (DR) type. The FPD has a detection surface in which a plurality of pixels are two-dimensionally arranged and a thin film transistor (TFT) panel (not illustrated) for driving the pixels. The radiation is incident on the detection surface of the detector through the image receiving surface 20A. The detector converts the incident radiation into an electric signal and outputs a radiographic image indicating the subject H on the basis of the converted electric signal. For example, the detector is an indirect conversion type that converts radiation into visible light using a scintillator and converts the converted visible light into an electric signal. In addition, the detector may be a direct conversion type that directly converts radiation into an electric signal. Further, the image receiving unit 20 may have any configuration other than the configuration using the FPD. For example, the image receiving unit 20 may have a configuration in which an image intensifier (II) and a camera are combined.

Further, the image receiving unit 20 is connected to, for example, the control unit 28 and a power circuit (not illustrated) of the main body portion 16 by a cable (not illustrated) including a signal line for transmitting a control signal and a power line for supplying power.

(Configuration of Carriage Portion)

Figure 4:
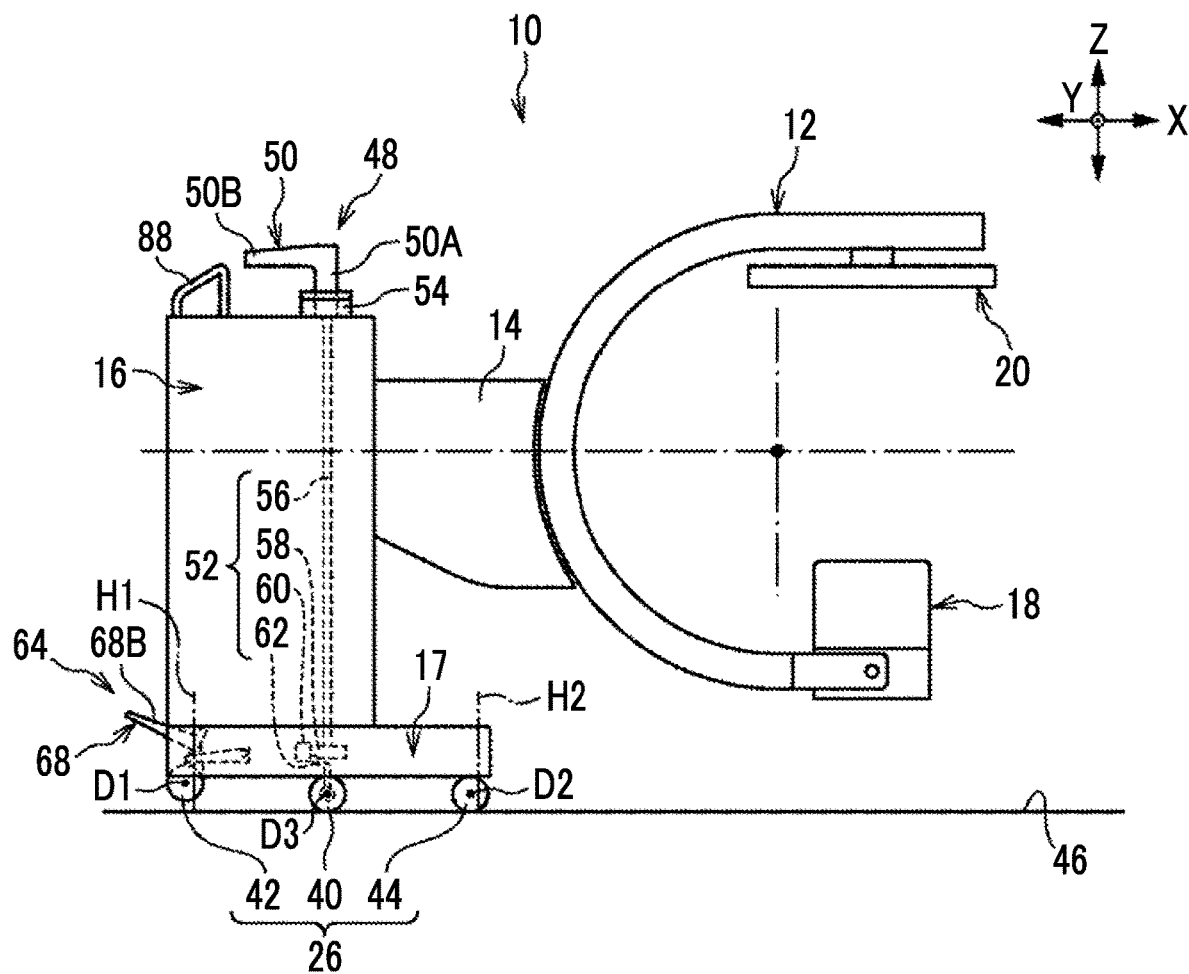
FIG. 4 is an overall side view illustrating a first grounded state of the mobile radiography apparatus according to an example of the embodiment.
Figure 5:
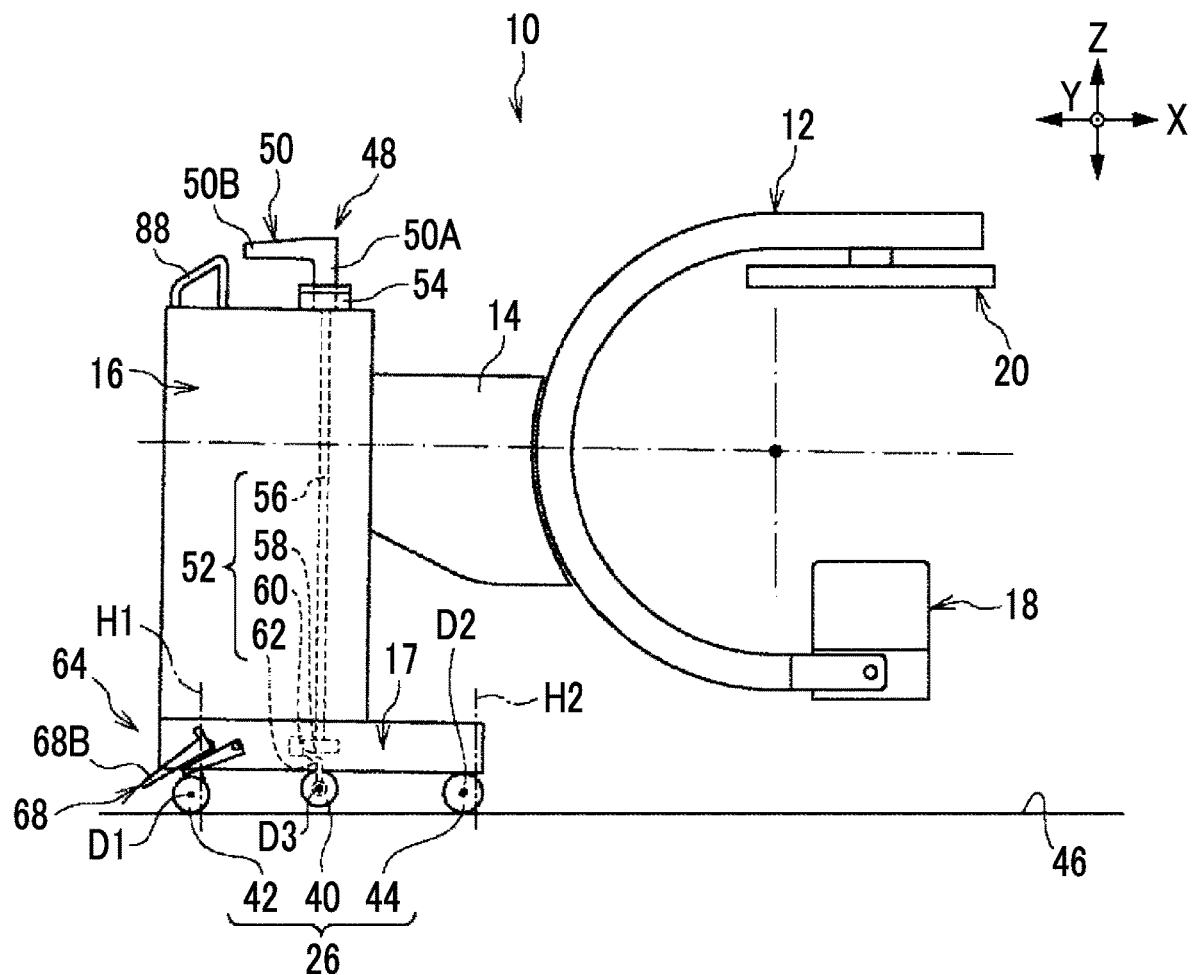
FIG. 5 is an overall side view illustrating a second grounded state of the mobile radiography apparatus according to an example of the embodiment.
Figure 6:
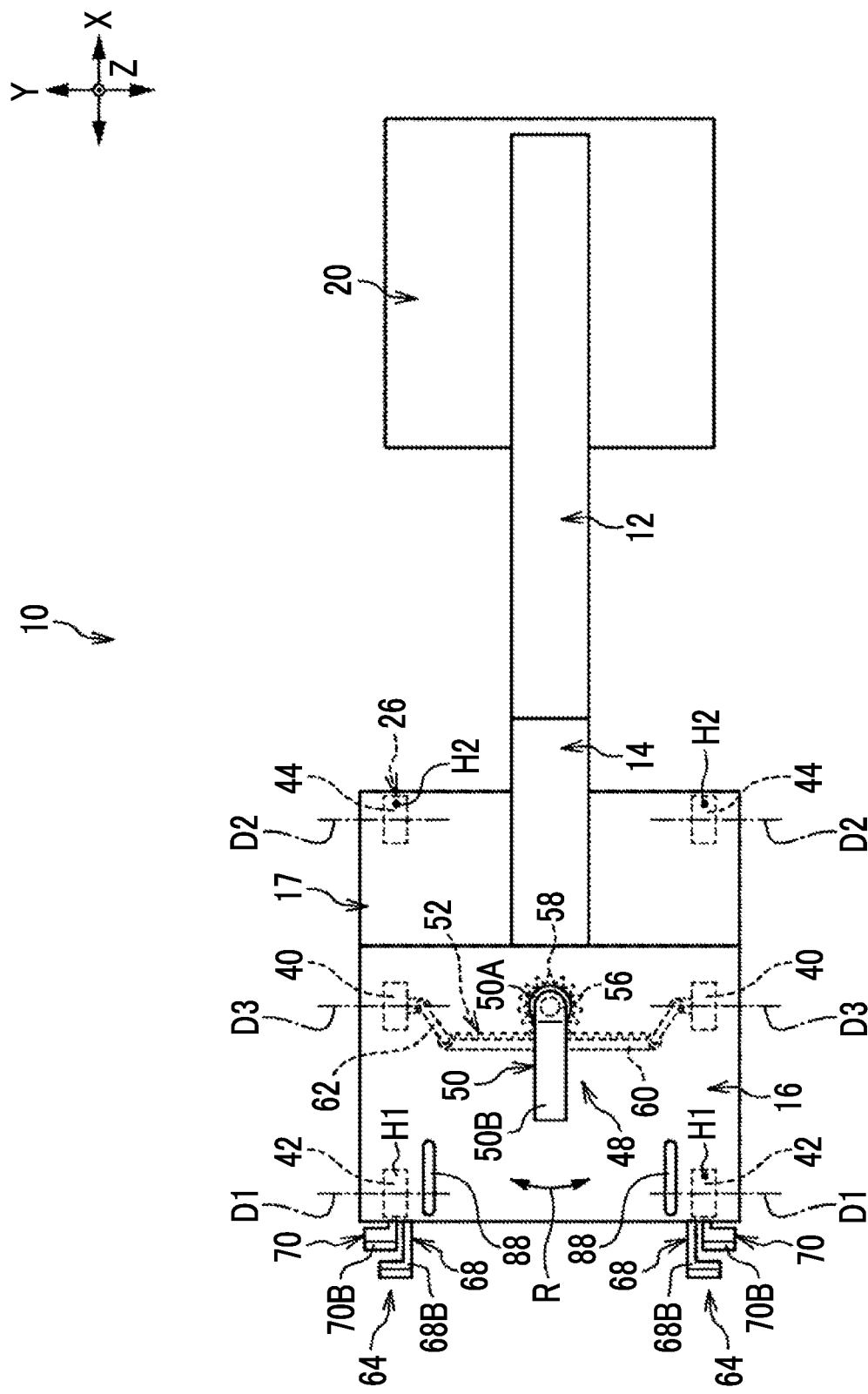
FIG. 6 is a plan view illustrating the mobile radiography apparatus according to an example of the embodiment.

As illustrated in FIGS. 4 to 6, the carriage portion 17 has a rectangular shape in a plan view and is attached to a lower surface of the main body portion 16. All of the main body portion 16, the arm 12, and the irradiation unit 18 and the image receiving unit 20 supported by the arm 12 of the mobile radiography apparatus 10 are mounted on the carriage portion 17.

The carriage portion 17 has a plurality of casters 26 provided in a lower part and can travel. Therefore, an operator pushes the mobile radiography apparatus 10 by hand such that the mobile radiography apparatus 10 can travel in, for example, an operating room or a ward.

As illustrated in FIG. 6, the casters 26 include a pair of steering casters 40, a pair of free casters 42, and a pair of always-grounded casters 44. That is, the carriage portion 17 has a total of six casters 26. The casters 26 are disposed in the carriage portion 17 in the order of the always-grounded casters 44, the steering casters 40, and the free casters 42 from the front to the rear of the carriage portion 17, that is, from the front to the rear of the mobile radiography apparatus 10.

Specifically, the pair of always-grounded casters 44 are provided in both end portions of the carriage portion 17 in the width direction (the Y direction in FIG. 6) in a front part of the carriage portion 17. Further, the pair of steering casters 40 are provided in both end portions of the carriage portion 17 in the width direction (the Y direction in FIG. 6) substantially at the center of the carriage portion 17 in the front-rear direction, that is, at the position of the center of gravity of the entire mobile radiography apparatus 10 in the front-rear direction. Furthermore, the pair of free casters 42 are provided in both end portions of the carriage portion 17 in the width direction (the Y direction in FIG. 6) in a rear part of the carriage portion 17.

The pair of free casters 42 are rotated independently about an axle D1 that extends in the horizontal direction (Y direction) and are turned independently about turning shafts H1 that extend in the vertical direction (Z direction). Further, the pair of free casters 42 are not connected to a steering 48 which is provided in the main body portion 16 and will be described below, and the steering angle of the free caster 42 is subordinately changed according to the direction of the force applied to the carriage portion 17.

The pair of always-grounded casters 44 are casters that are always grounded to a floor 46 illustrated in FIG. 4. Here, the term "always" means that the caster is grounded in both a first grounded state and a second grounded state which will be described below. Therefore, for example, in a case in which the carriage portion 17 is inclined, the always-grounded casters 44 are also separated from the floor 46. In this embodiment, the always-grounded casters 44 have the same configuration as the free casters 42. That is, the pair of always-grounded casters 44 are rotated independently about an axle D2 that extends in the horizontal direction (Y direction) and are turned independently about turning shafts H2 that extend in the vertical direction (Z direction). Then, similarly to the free caster 42, the steering angle of the always-grounded caster 44 is subordinately changed according to the direction of the force applied to the carriage portion 17.

The pair of steering casters 40 are rotated independently about an axle D3 that extends in the horizontal direction (Y direction). In addition, the pair of steering casters 40 are connected to the steering 48 which is provided in the main body portion 16 and will be described below, and the steering angle of the steering caster 40 is given by the operation of the steering 48. The pair of steering casters 40 are turned in the same direction in operative association with each other by the operation of the steering 48.

(Configuration of Steering)

As illustrated in FIGS. 4 to 6, the main body portion 16 is provided with the steering 48 that gives a steering angle to the steering casters 40. The steering 48 comprises a lever 50 and a link mechanism 52 that transmits the rotation of the lever 50 to the pair of steering casters 40.

As illustrated in FIGS. 4 and 5, the lever 50 is attached to the main body portion 16 through, for example, a base 54 fixed to an upper surface of the main body portion 16. The lever 50 is vertically provided on the base 54 and comprises a rotation shaft 50A that is attached to the base 54 so as to be rotatable about an axis line and a grip portion 50B that extends from the rotation shaft 50A outward (horizontally) in a radial direction of the rotation shaft 50A. The operator holds the grip portion 50B by hand and rotates the grip portion 50B about the axis line of the rotation shaft 50A to operate the lever 50.

The lever 50 can be rotated about the axis line of the rotation shaft 50A in a range of about 90° to the left and right from a reference position where the grip portion 50B of the lever 50 extends in the front-rear direction (X direction) of the mobile radiography apparatus 10. The rotation angle of the lever 50 can be adjusted to any angle within a rotatable range.

The link mechanism 52 comprises a shaft 56 having an upper end fixed to the rotation shaft 50A of the lever 50, a pinion 58 that is fixed to a lower end of the shaft 56, a rack 60 that is engaged with the pinion 58, and a tie rod 62 that connects the rack 60 and the steering casters 40.

In a case in which the operator rotates the grip portion 50B of the lever 50 to the left and the right (in the direction of an arrow R in FIG. 6) about the axis line of the rotation shaft 50A, the rotation shaft 50A of the lever 50 is rotated about the axis line, and the shaft 56 of the link mechanism 52 fixed to the rotation shaft 50A and the pinion 58 fixed to the shaft 56 are rotated with the rotation of the rotation shaft 50A. In a case in which the pinion 58 is rotated, the rack 60 engaged with the pinion 58 is moved in the width direction (the Y direction in FIG. 6) of the carriage portion 17 in operative association with the rotation of the pinion 58. The movement of the rack 60 is transmitted to the steering casters 40 through the tie rod 62, and the steering casters 40 are turned.

Specifically, as illustrated in FIG. 7A, in a case in which the lever 50 is rotated in the left direction (the direction of an arrow R1), the rack 60 of the link mechanism 52 is moved to the left (arrow Y1), and each of the pair of steering casters 40 is rotated in the right direction (the direction of an arrow 51). This makes it possible to move the carriage portion 17 in the right direction.

On the other hand, as illustrated in FIG. 7B, in a case in which the lever 50 is rotated in the right direction (the direction of an arrow R2), the rack 60 of the link mechanism 52 is moved to the right (the direction of an arrow Y2), and each of the pair of steering casters 40 is moved in the left direction (arrow S2). This makes it possible to move the carriage portion 17 in the left direction.

(Configuration of Switching Mechanism)

Further, as illustrated in FIGS. 4 to 6, the carriage portion 17 is provided with a switching mechanism 64. The switching mechanism 64 raises and lowers the free casters 42 with respect to the steering casters 40 to selectively switch between the first grounded state and the second grounded state.

Here, the first grounded state is a grounded state in which the free casters 42 are separated from the floor 46 and the steering casters 40 are grounded to the floor 46 as illustrated in FIG. 4. In addition, the second grounded state is a grounded state in which the free casters 42 are grounded to the floor 46 and the steering casters 40 are separated from the floor 46 as illustrated in FIG. 5.

Figure 8:
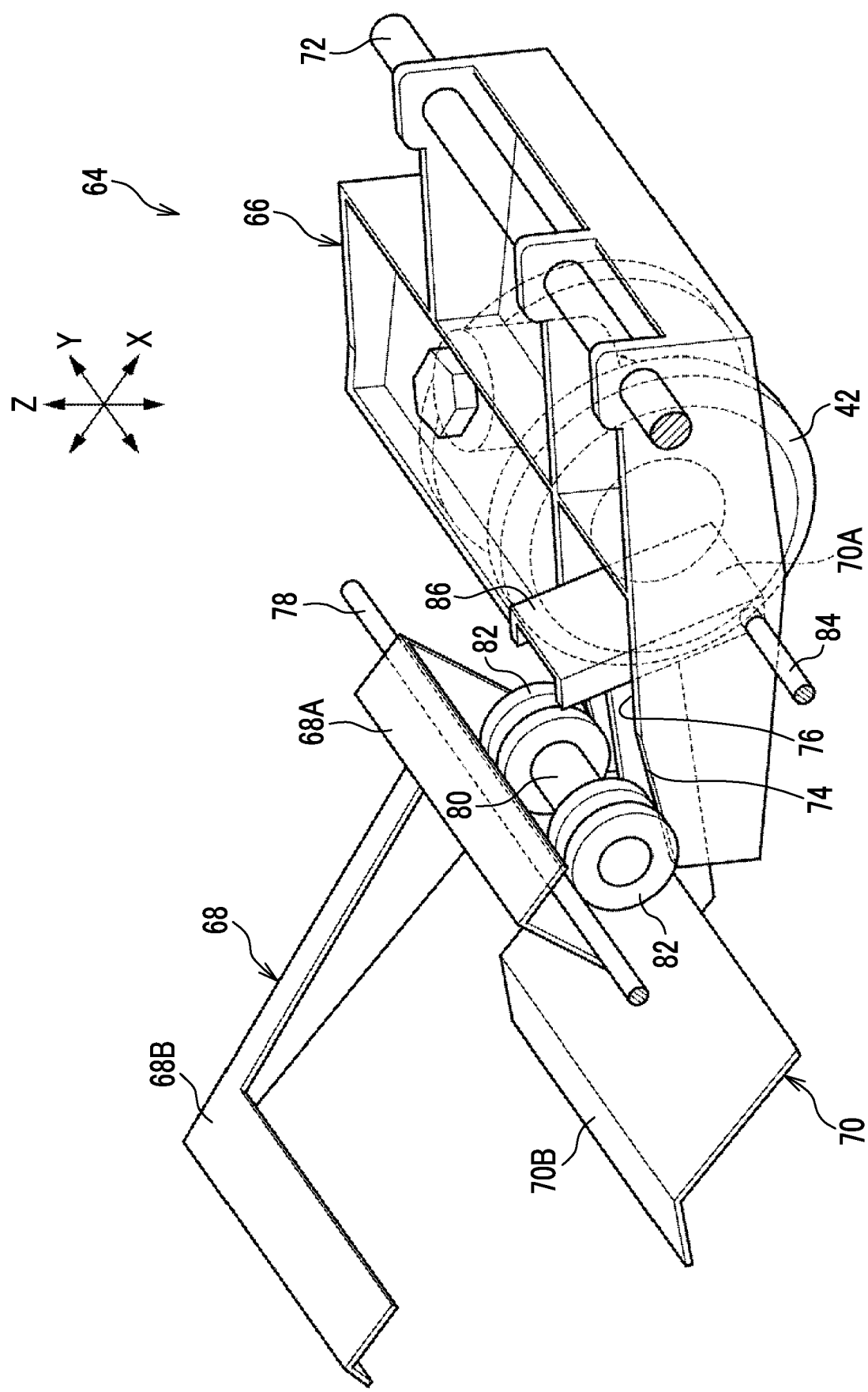
FIG. 8 is a perspective view illustrating a switching mechanism of the mobile radiography apparatus according to an example of the embodiment.
Figure 9:
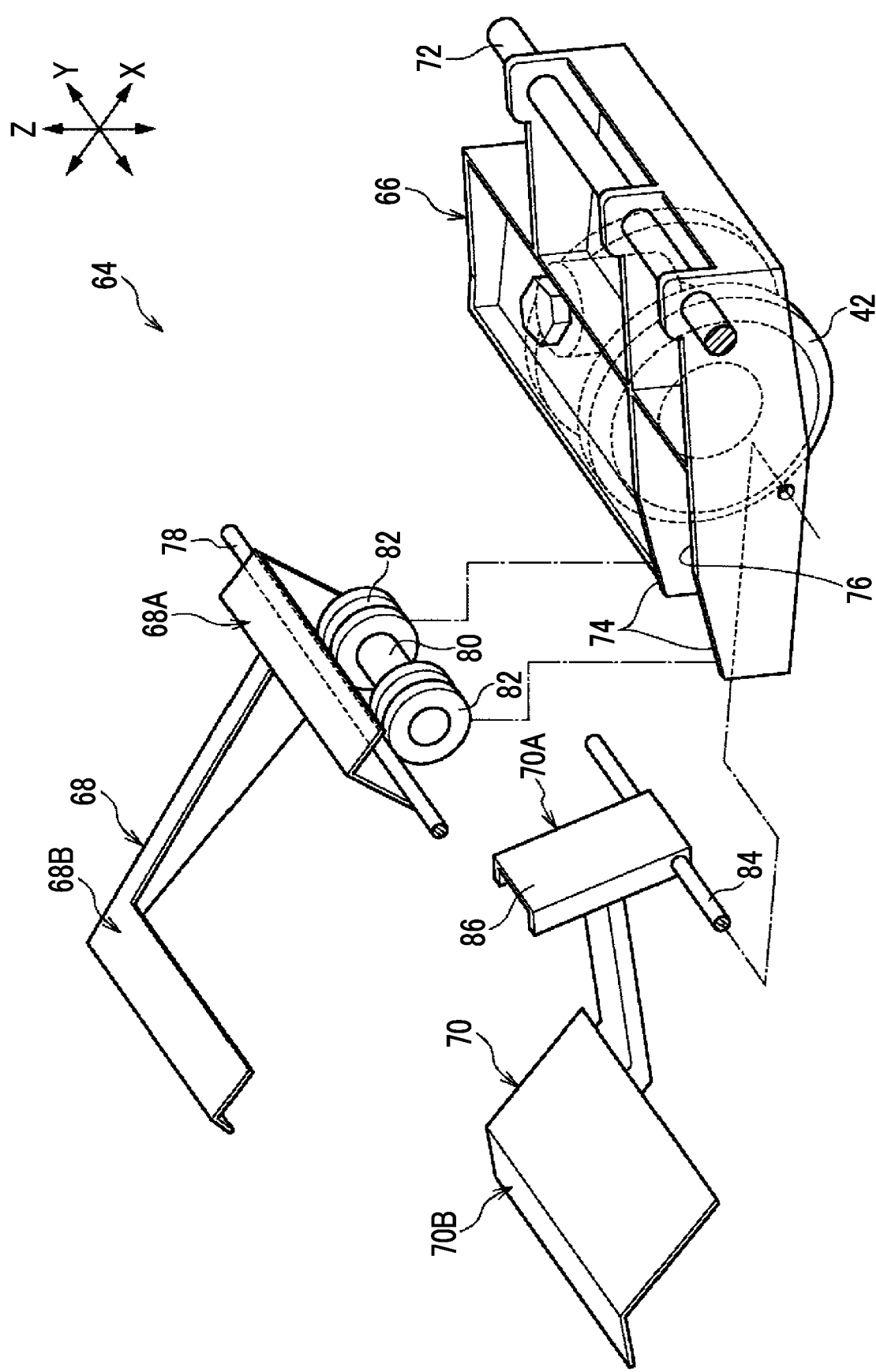
FIG. 9 is an exploded perspective view illustrating the switching mechanism illustrated in FIG. 8.

Specifically, as illustrated in FIGS. 8 and 9, the switching mechanism 64 comprises a movable frame 66, and a first pedal 68 and a second pedal 70 as pedals for raising and lowering the free caster 42.

A front end portion (an end portion on the front side) of the movable frame 66 is fixed to a shaft 72 through a bearing portion (not illustrated) so as to be rotatable about an axis line of the shaft 72. The shaft 72 extends in the width direction (Y direction) of the carriage portion 17 illustrated in FIG. 4, and both ends of the shaft 72 in the axial direction are fixed to the carriage portion 17. On the other hand, the free caster 42 is attached to a rear end portion (an end portion on the rear side) of the movable frame 66. That is, the free caster 42 is attached to the carriage portion 17 through the movable frame 66.

The movable frame 66 is rotated about the shaft 72 provided in the front end portion. The rear end portion of the movable frame 66 is moved up and down in the vertical direction (Z direction) by the rotation about the shaft 72 while drawing an arc. In addition, the rear end portion of the movable frame 66 is biased upward in the vertical direction (Z direction) by a biasing member (not illustrated).

Further, a pair of slopes 74 are formed on an upper surface of the rear end portion of the movable frame 66. The height of the pair of slopes 74 gradually increases from the rear end portion to the front end portion of the movable frame 66. Further, a groove 76 is formed between the pair of slopes 74.

The first pedal 68 comprises a base portion 68A that is provided in a front end portion (an end portion on the front side) of the first pedal 68 and a tread 68B that is provided in a rear end portion (an end portion on the rear side) of the first pedal 68. The base portion 68A is fixed to a shaft 78 through a bearing portion (not illustrated) so as to be rotatable about an axis line of the shaft 78. The shaft 78 extends in the width direction (Y direction) of the carriage portion 17 illustrated in FIG. 4, and both end portions of the shaft 78 in the axial direction are fixed to the carriage portion 17.

Further, a bearing shaft 80 that extends in parallel to the shaft 78 is fixed to a lower portion of the shaft 78 in the base portion 68A of the first pedal 68. A pair of bearings 82 are fixed to the bearing shaft 80 so as to be rotatable about an axis line of the bearing shaft 80.

The pair of bearings 82 can be rotated coaxially and are provided at an interval in the axial direction of the bearing shaft 80. Further, the pair of bearings 82 are mounted on the pair of slopes 74 formed in the movable frame 66 so as to be movable along the slopes 74.

The tread 68B of the first pedal 68 is integrally fixed to the base 68A and can be rotated about the axis line of the shaft 78 together with the base 68A. In addition, as illustrated in FIGS. 4 to 6, the tread 68B of the first pedal 68 protrudes to the rear side of the carriage portion 17. This enables the operator to step on the tread 68B of the first pedal 68 from the outside of the mobile radiography apparatus 10.

As illustrated in FIGS. 8 and 9, the second pedal 70 comprises a base portion 70A that is provided in a front end portion (an end portion on the front side) of the second pedal 70 and a tread 70B that is provided in a rear end portion (an end portion on the rear side) of the second pedal 70. The base portion 70A is disposed in the groove 76 formed between the pair of slopes 74 of the movable frame 66 and is fixed to a shaft 84 through a bearing portion (not illustrated) so as to be rotatable about an axis line of the shaft 84. The shaft 84 extends in the width direction (Y direction) of the carriage portion 17 illustrated in FIG. 4, and both end portions of the shaft 84 in the axial direction are fixed to the movable frame 66.

Further, a contact portion 86 is provided above the shaft 84 in the base portion 70A of the second pedal 70. The contact portion 86 protrudes upward from the groove 76 of the movable frame 66 in the vertical direction (Z direction) and is located between the pair of slopes 74. Therefore, the contact portion 86 can come into contact with the pair of bearings 82 moved on the pair of slopes 74.

The tread 70B of the second pedal 70 is integrally fixed to the base portion 70A and can be rotated about the axis line of the shaft 84 together with the base portion 70A. Further, as illustrated in FIG. 6, the tread 70B of the second pedal 70 protrudes to the rear side of the carriage portion 17, similarly to the tread 68B of the first pedal 68. This enables the operator to step on the tread 70B of the second pedal 70 from the outside of the mobile radiography apparatus 10.

Figure 10:
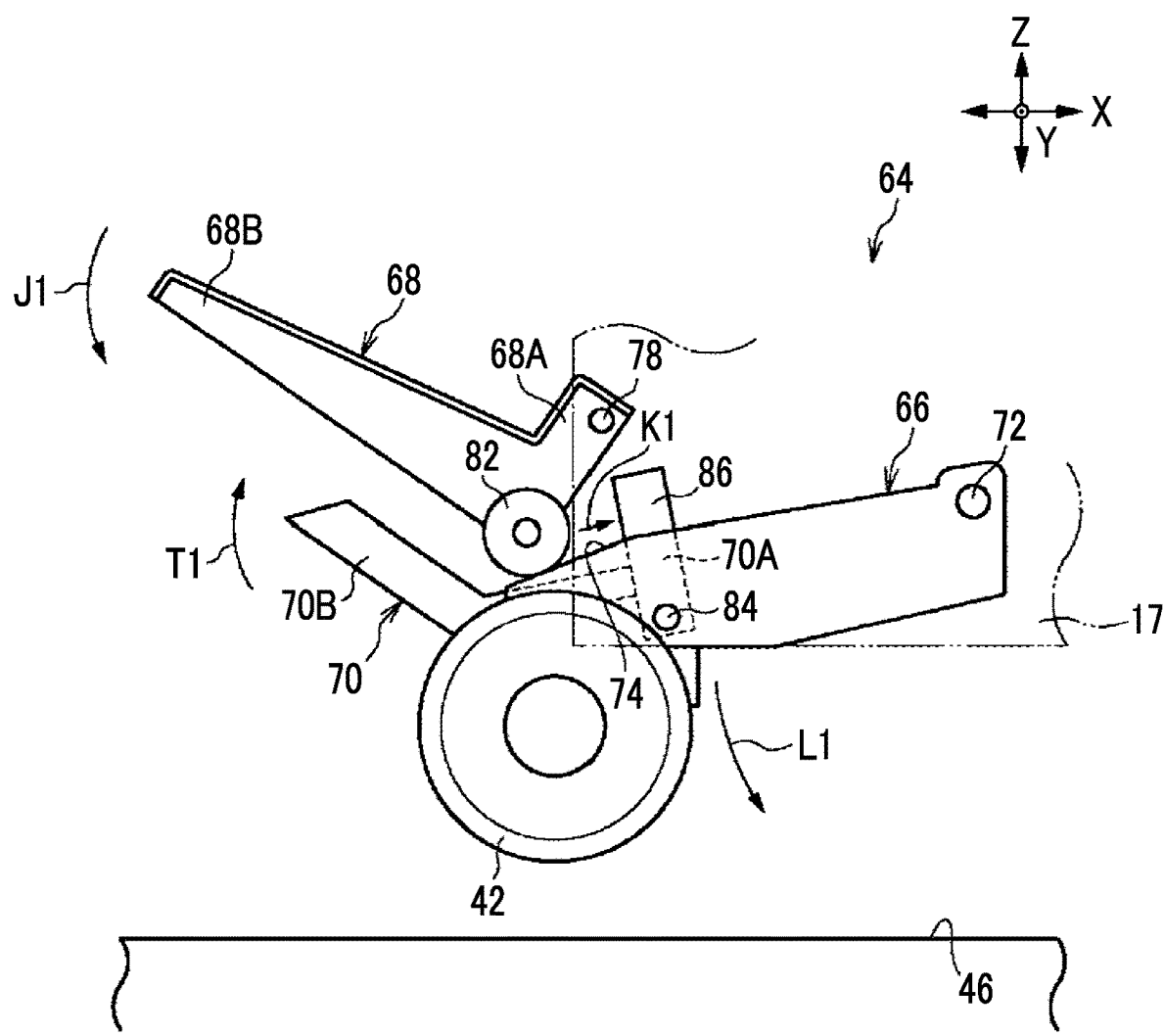
FIG. 10 is a side view illustrating the switching mechanism in the first grounded state.

In a case in which the grounded state is switched from the first grounded state to the second grounded state, the operator steps on the tread 68B of the first pedal 68 to lower the free caster 42 with respect to the steering caster 40. Specifically, as illustrated in FIG. 10, in a case in which the operator steps on the tread 68B of the first pedal 68, the first pedal 68 is rotated about the axis line of the shaft 78 in the direction of an arrow J1 (counterclockwise in FIG. 10). In this case, the bearings 82 provided in the base portion 68A of the first pedal 68 are moved forward (in the direction of an arrow K1 in FIG. 10) along the slopes 74 of the movable frame 66.

The height of the slopes 74 gradually increases from the rear end portion to the front end portion of the movable frame 66. Therefore, in a case in which the bearings 82 are moved forward, the slopes 74 are pushed down in the vertical direction (Z direction) by the bearings 82. Then, the movable frame 66 is rotated about the axis line of the shaft 72 in the direction of an arrow L1 (counterclockwise in FIG. 10), and the rear end portion of the movable frame 66 is lowered.

Figure 11:
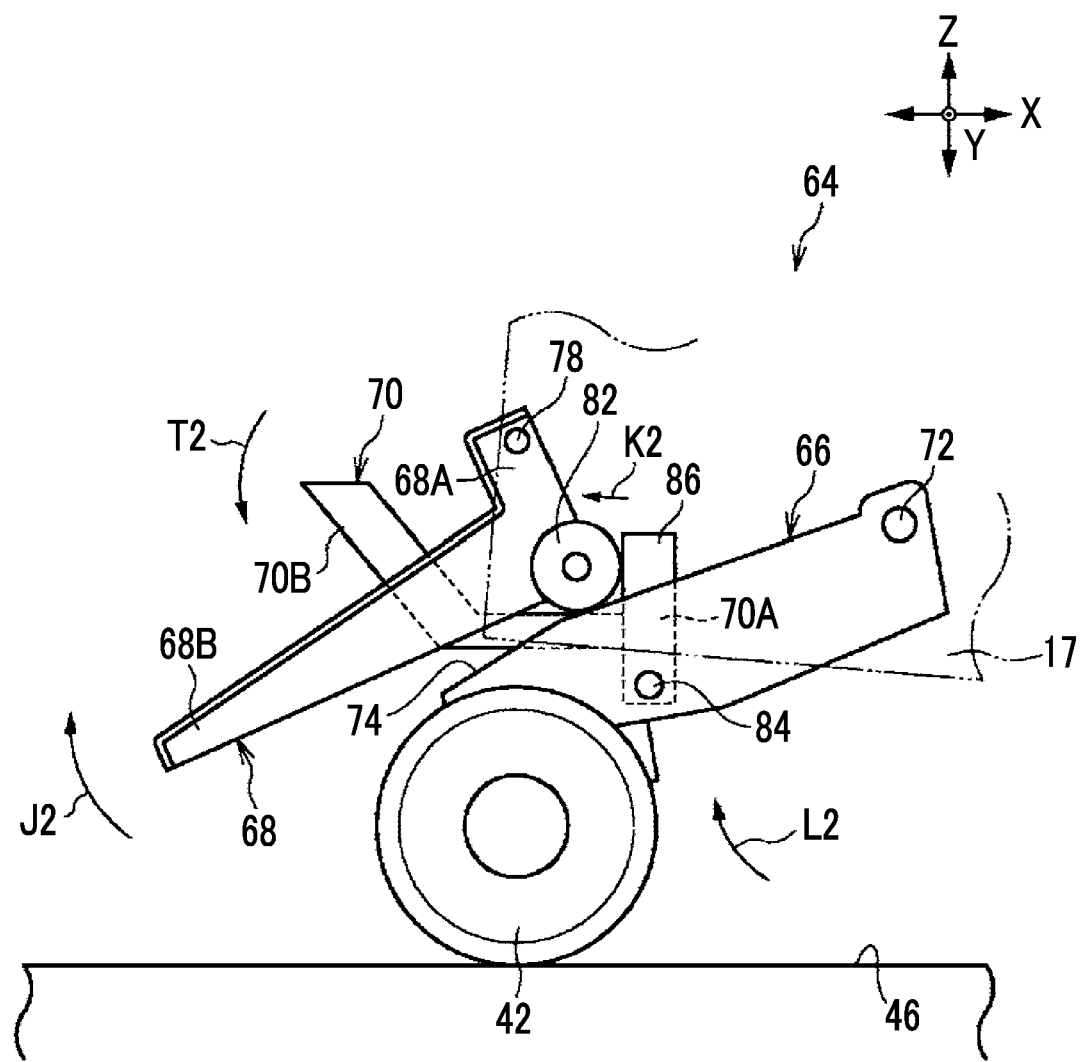
FIG. 11 is a side view illustrating the switching mechanism in the second grounded state.

Further, in a case in which the bearings 82 of the first pedal 68 are moved forward along the slopes 74 of the movable frame 66, the bearings 82 come into contact with the contact portion 86 of the second pedal 70 which is provided between the pair of slopes 74 (see FIG. 11). In a case in which the contact portion 86 is pushed forward by the bearings 82, the second pedal 70 is rotated about the axis line of the shaft 84 in the direction of an arrow T1 (clockwise in FIG. 10). Then, the tread 70B of the second pedal 70 is raised and is located above the tread 68B of the first pedal 68 in the vertical direction (Z direction) (see FIG. 11).

The free caster 42 is attached to the lower surface of the rear end portion of the movable frame 66. Therefore, in a case in which the rear end portion of the movable frame 66 is lowered, the free caster 42 is lowered with respect to the carriage portion 17, that is, the steering caster 40 illustrated in FIG. 5. Then, as illustrated in FIGS. 5 and 11, the free caster 42 is grounded to the floor 46. In addition, the free caster 42 is located below the steering caster 40. Therefore, the steering caster 40 is separated from the floor 46.

On the other hand, in a case in which the grounded state is switched from the second grounded state to the first grounded state, the operator steps on the tread 70B of the second pedal 70 to raise the free caster 42 with respect to the steering caster 40. Specifically, as illustrated in FIG. 11, in a case in which the operator steps on the tread 70B of the second pedal 70, the second pedal 70 is rotated about the axis line of the shaft 84 in the direction of an arrow T2 (counterclockwise in FIG. 11). In this case, the contact portion 86 provided in the base portion 70A of the second pedal 70 is also rotated about the axis line of the shaft 84 in the direction of the arrow T2.

In a case in which the contact portion 86 is moved in the direction of the arrow T2, the bearing 82 of the first pedal 68 is pushed by the contact portion 86, and the first pedal 68 is rotated about the axis line of the shaft 78 in the direction of an arrow J2 (clockwise in FIG. 11). Then, the bearing 82 is moved backward (in the direction of an arrow K2 in FIG. 11) along the slope 74 of the movable frame 66, and the tread 68B of the first pedal 68 is raised.

In a case in which the bearing 82 is moved backward, the slope 74 pushed down in the vertical direction (Z direction) by the bearing 82 is raised upward in the vertical direction (Z direction) by the biasing force of a biasing member (not illustrated). Then, the movable frame 66 is rotated about the axis line of the shaft 72 in the direction of an arrow L2 (clockwise in FIG. 11), and the rear end portion of the movable frame 66 is raised.

The free caster 42 is attached to the lower surface of the rear end portion of the movable frame 66. Therefore, as the rear end portion of the movable frame 66 is raised, the free caster 42 is raised with respect to the carriage portion 17, that is, the steering caster 40 illustrated in FIG. 4. Then, as illustrated in FIGS. 4 and 10, the free casters 42 are separated from the floor 46. In addition, the free casters 42 are located above the steering casters 40. Therefore, the steering casters 40 are grounded to the floor 46.

(Configuration of Handle)

Further, as illustrated in FIGS. 4 and 5, a pair of handles 88 for pushing and pulling the main body portion 16 (carriage portion 17) are fixed to the upper surface of the main body portion 16. The handle 88 is, for example, a bar handle that is composed of a cylindrical bar having a substantially circular shape in a cross-sectional view.

The handle 88 extends in the front-rear direction (X direction) of the main body portion 16, and both end portions of the handle 88 in an extending direction are fixed to the upper surface of the main body portion 16. Further, as illustrated in FIG. 6, the pair of handles 88 are provided in both end portions in the width direction (the Y direction in FIG. 6) in the rear part of the main body portion 16.

The pair of handles 88 are held and pushed and pulled by the operator in a case in which the mobile radiography apparatus 10 is moved. In addition, for example, the shape and fixation position of the handle 88 are not limited to the embodiment, and a shape that is easy to grip and a position that is easy to grip are appropriately selected.

(Configuration of Steering Lock Mechanism)

Figure 12A:
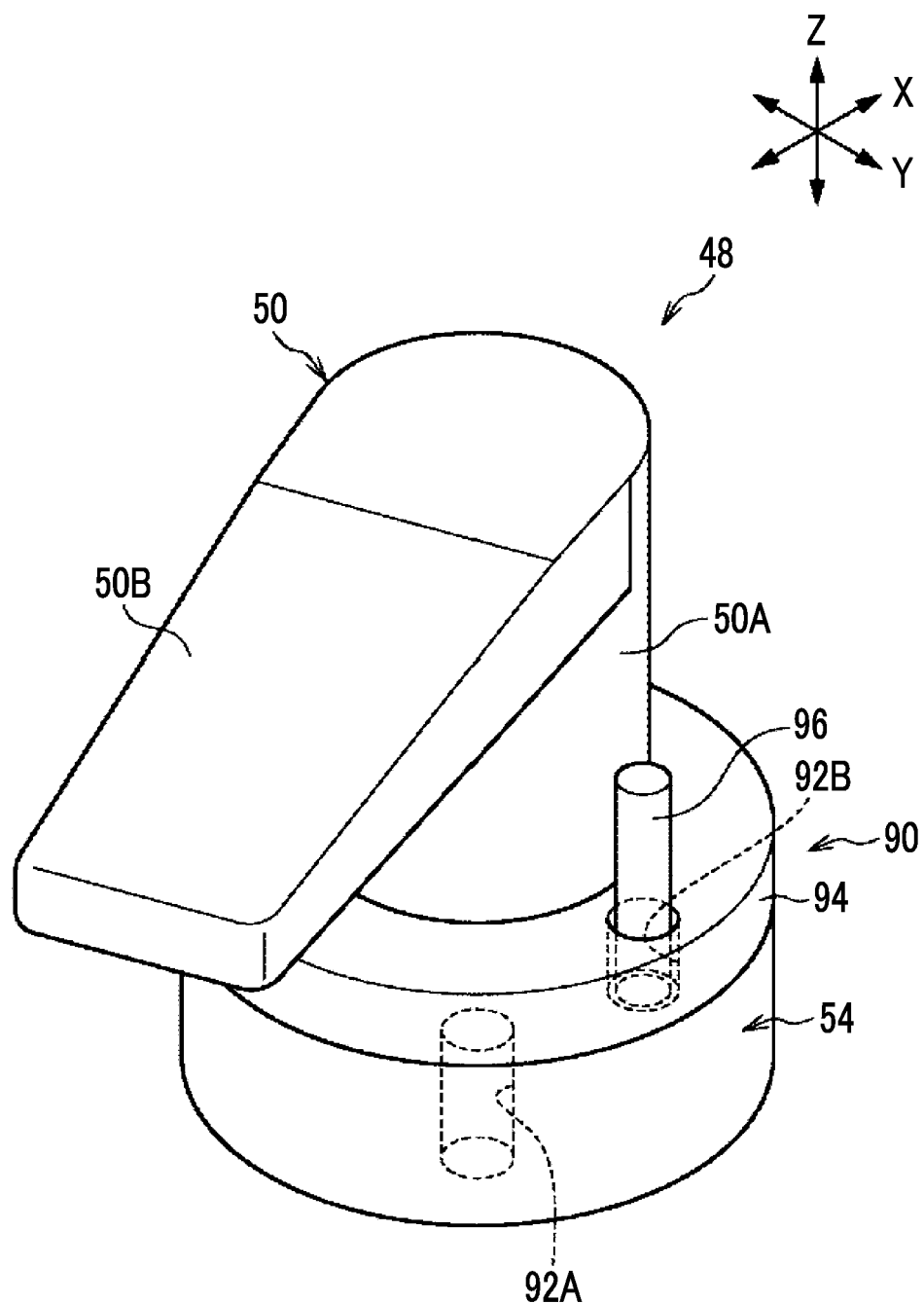
FIG. 12A is a perspective view illustrating an unlocked state of the steering by the steering lock mechanism.
Figure 12B:
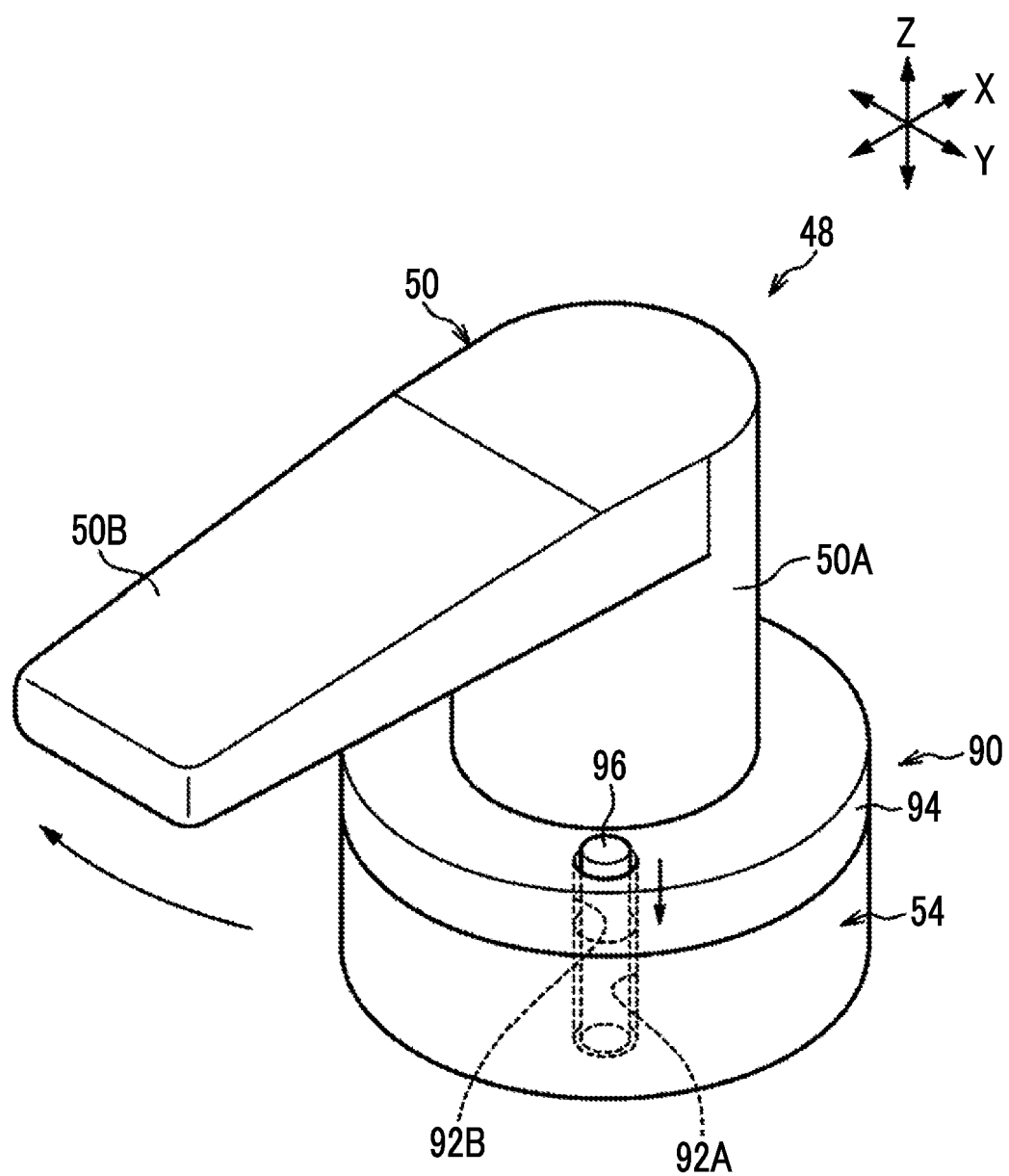
FIG. 12B is a perspective view illustrating a locked state of the steering by the steering lock mechanism.

Further, as illustrated in FIGS. 12A and 12B, the steering 48 is provided with a steering lock mechanism 90 that locks the operation by the steering 48 in the second grounded state in which the steering casters 40 illustrated in FIG. 4 are separated from the floor 46.

In this embodiment, for example, the steering lock mechanism 90 locks the rotation of the lever 50 constituting the steering 48 with respect to the base 54. Specifically, the steering lock mechanism 90 comprises a pin hole 92A that is formed in the upper surface of the base 54, a pin hole 92B that is formed in a flange portion 94 which is a contact portion with the base 54 of the lever 50, and a locking pin 96 that is inserted into the pin hole 92B of the lever 50. The pin hole 92B in the flange portion 94 of the lever 50 has substantially the same diameter as the pin hole 92A of the base 54 and passes through the flange portion 94 in the vertical direction (Z direction).

Here, for example, the pin hole 92B of the lever 50 is formed at a position that communicates with the pin hole 92A of the base 54 in a case in which the grip portion 50B of the lever 50 is located at the reference position (the position where the grip portion 50B of the lever 50 extends in the front-rear direction (X direction) of the mobile radiography apparatus 10).

As illustrated in FIG. 12A, in a state in which the pin hole 92A of the base 54 and the pin hole 92B of the lever 50 do not communicate with each other, that is, in a state in which the grip portion 50B of the lever 50 is not located at the reference position, the locking pin 96 inserted into the pin hole 92B of the lever 50 is not capable of being inserted into the pin hole 92A of the base 54.

Therefore, the lever 50 can be rotated about the axis line of the rotation shaft 50A with respect to the base 54. In this case, the steering casters 40 (see FIG. 4) can be operated by the lever 50 constituting the steering 48.

On the other hand, as illustrated in FIG. 12B, in a state in which the pin hole 92A of the base 54 and the pin hole 92B of the lever 50 communicate with each other, that is, in a state in which the grip portion 50B of the lever 50 is located at the reference position, the locking pin 96 inserted into the pin hole 92B of the lever 50 can be inserted into the pin hole 92A of the base 54.

Therefore, the lever 50 is not rotatable with respect to the base 54 by pushing the locking pin 96 from the upper side such that the tip of the locking pin 96 is located inside the pin hole 92A of the base 54. In this case, the operation of the steering casters 40 (see FIG. 4) by the steering 48 is locked. In addition, the locking pin 96 may be manually inserted into the pin hole 92A or may be electrically inserted into the pin hole 92A by, for example, a solenoid (not illustrated).

(Operation and Effect)

According to the mobile radiography apparatus 10 of this embodiment, the carriage portion 17 is provided with the steering casters 40 whose steering angle is given by the operation of the steering 48 and the free casters 42 whose steering angle is changed subordinately according to the direction of the force applied to the carriage portion 17. Further, the switching mechanism 64 can selectively switch the casters 26 between the first grounded state and the second grounded state.

Therefore, the switching mechanism 64 selectively switches the grounded state of the free casters 42 and the steering casters 40 to change the operability of the carriage portion 17 according to the usage situation.

That is, the traveling direction of the carriage portion 17 can be fixed by changing the grounded state to the first grounded state in which the free casters 42 are separated from the floor 46 and the steering casters 40 are grounded to the floor 46. In a case in which the traveling direction of the carriage portion 17 can be fixed, it is convenient to perform continuous imaging while moving the imaging position.

For example, in a case in which imaging is performed while an imaging part is changed along the body axis direction of the subject H, it is convenient that the carriage portion 17 can be stably moved along the body axis direction of the subject H. The steering angle of the steering casters 40 can be fixed by the operation of the steering 48. Therefore, in a case in which the carriage portion 17 is moved, the carriage portion 17 does not wobble, and the traveling direction is stable.

On the other hand, the carriage portion 17 is turned in a small radius by changing the grounded state to the second grounded state in which the free casters 42 are grounded to the floor 46 and the steering casters 40 are separated from the floor 46. In a case in which the carriage portion 17 is turned in a small radius, it is possible to change the direction of the carriage portion 17 in a narrow space. Therefore, it is convenient that the mobile radiography apparatus 10 is used in a narrow hospital room.

Further, since the switching mechanism 64 switches the grounded state of the free casters 42 and the steering casters 40, the configuration is simple. For example, as the switching mechanism, a method is considered which switches between a valid state and an invalid state of the input of an operating force from the steering 48 to the steering casters 40 in a state in which the steering casters 40 are grounded.

The invalid state is, in short, a state in which the steering casters 40 function as the free casters. It is easier to simplify the configuration of the mechanism for switching the grounded state than the configuration of the mechanism for switching between the valid state and the invalid state of the input of the operating force from the steering 48 as described above.

Furthermore, according to this embodiment, the switching mechanism 64 raises and lowers the free casters 42 with respect to the steering casters 40 to switch between the first grounded state and the second grounded state. In general, since the steering casters 40 are connected to the steering 48, the weight of the steering casters 40 is larger than that of the free casters 42. According to this embodiment, since the switching mechanism 64 raises and lowers the free caster 42, it is possible to easily switch the grounded state of the casters 26 with a small force, as compared to a configuration in which the steering casters 40 are raised and lowered.

Moreover, the switching mechanism 64 has the first pedal 68 and the second pedal 70 as the pedal for raising and lowering the free casters 42. Therefore, since the operator steps on the first pedal 68 or the second pedal 70 to raise and lower the free casters 42, it is possible to switch the grounded state of the casters 26 while manually operating the mobile radiography apparatus 10.

In particular, according to this embodiment, the pedal includes two pedals of the first pedal 68 and the second pedal 70. In a case in which one of the pedals is lowered, the other pedal is raised. In general, in a case in which the free casters 42 are raised and lowered by one pedal, the pedal is lowered to move the free casters 42 down, and the pedal is raised to move the free casters 42 up. However, the load on the operation of pulling up the pedal larger than that on the operation of pushing the pedal down.

Here, according to this embodiment, the two pedals are combined such that both the operation of raising the free casters 42 and the operation of lowering the free casters 42 can be achieved by stepping on (depressing) the pedal. Therefore, it is easy to switch the grounded state of the casters 26.

Further, in this embodiment, the carriage portion 17 is provided with the always-grounded casters 44 that are grounded to the floor 46 in both the first grounded state and the second grounded state, in addition to the free casters 42 and the steering casters 40.

Therefore, even in a case in which one of the free casters 42 and the steering casters 40 is separated from the floor 46, the carriage portion 17 can travel stably. In addition, in a case in which the grounded state of the free casters 42 and the steering casters 40 is switched, it is possible to suppress the postural instability of the carriage portion 17.

Further, according to this embodiment, the always-grounded casters 44, the steering casters 40, and the free casters 42 are disposed in this order from the front to the rear of the carriage portion 17. As described above, since the steering casters 40 are disposed between the always-grounded casters 44 and the free casters 42, the steering casters 40 can be disposed at a position close to the position of the center of gravity of the main body portion 16. Therefore, it is possible to suppress the postural instability of the main body portion 16 in a case in which the steering 48 is operated.

In particular, according to this embodiment, the steering casters 40 are disposed at the position of the center of gravity of the entire mobile radiography apparatus 10 in the front-rear direction of the carriage portion 17. Therefore, it is possible to further suppress the postural instability of the main body portion 16 in a case in which the steering 48 is operated.

Further, the arm 12 of the mobile radiography apparatus 10 according to this embodiment has two end portions. The irradiation unit 18 is provided at one end, and the image receiving unit 20 is provided at the other end. Therefore, the irradiation unit 18 and the image receiving unit 20 can be integrally held by the arm 12. This configuration makes it possible to perform imaging while moving the carriage portion 17 in the body axis direction of the subject H, for example, during surgery.

Furthermore, the mobile radiography apparatus 10 according to this embodiment includes the steering lock mechanism 90 that locks the operation by the steering 48. Therefore, for example, in the second grounded state in which the steering casters 40 are separated from the floor 46, the steering lock mechanism 90 prevents the lever 50 from being rotated with respect to the base 54 (main body portion 16), which makes it possible to prevent the rotation of the steering casters 40. As a result, it is possible to suppress the postural instability of the mobile radiography apparatus 10 caused by the movement of the steering casters 40 in a case in which the main body portion 16 is moved by the free casters 42.

Further, according to this embodiment, the handle 88 for pushing and pulling the carriage portion 17 is provided separately from the lever 50 constituting the steering 48. As described above, since the handle 88 is provided separately from the lever 50, it is easy to operate in a case in which the carriage portion 17 is moved by the free casters 42.

<Other Embodiments>

An example of the embodiment of the present disclosure has been described above. However, the present disclosure is not limited to the above-described embodiment, and various modifications and changes can be made without departing from the gist of the present disclosure.

For example, in the above-described embodiment, the always-grounded caster 44 is a caster whose steering angle is changed subordinately, similarly to the free caster 42. However, the always-grounded caster 44 may be a fixed caster that is not capable of being turned.

In addition, the carriage portion 17 is not necessarily provided with the always-grounded casters 44. In a case in which the always-grounded casters 44 are not provided, for example, three or more steering casters 40 and three or more free casters 42 are provided in the carriage portion 17 to stably move the carriage portion 17. Further, the disposition of each of the casters 26 is not limited to the above-described embodiment. For example, the steering casters 40 may be disposed behind the always-grounded casters 44 and the free casters 42.

Furthermore, in the above-described embodiment, the free casters 42 are raised and lowered by the switching mechanism 64. However, the steering casters 40 may be raised and lowered by the switching mechanism 64.

Moreover, in the above-described embodiment, the handle 88 is provided on the upper surface of the main body portion 16. However, the handle 88 may not be provided, and the lever 50 of the steering 48 may be pushed and pulled or the main body portion 16 may be directly pushed and pulled to move the mobile radiography apparatus 10.

In addition, in the above-described embodiment, the link mechanism 52 of the steering 48 is configured to include the shaft 56, the pinion 58, the rack 60, and the tie rod 62. However, the configuration of the link mechanism 52 is not limited to the above-described embodiment, and it is possible to use other known link mechanisms.

Further, in the above-described embodiment, the steering lock mechanism 90 is configured to lock the rotation of the lever 50 constituting the steering 48. However, the steering lock mechanism 90 may be configured to lock the rotation of any of the mechanisms constituting the steering 48 and the steering casters 40 and may be, for example, a stopper that locks the turning of the steering casters 40.

Furthermore, in a case in which the steering casters 40 can be allowed to be moved in the movement of the main body portion 16 by the free casters 42, the steering lock mechanism 90 is not necessarily provided.

Moreover, in the above-described embodiment, the C-arm having a C-shape in a side view has been described as an example of the arm 12. However, a U-arm having a U-shape in a side view may be used. In addition, the arm 12 may be an I-arm having an I-shape in a side view in which only the irradiation unit 18 is provided at one end.

Further, in the above-described embodiment, the irradiation unit 18 and the image receiving unit 20 are provided at both ends of the arm 12. However, the image receiving unit 20 may not necessarily be provided in the arm 12, and at least only the irradiation unit 18 may be provided in the arm 12.

In addition, in the above-described embodiment, X-rays have been described as an example of the radiation. However, the radiation is not limited to the X-rays and may be, for example, γ-rays.

The disclosure of JP2019-199331 filed on Oct. 31, 2019 is incorporated herein by reference in its entirety. All of the documents, patent applications, and technical standards described in the specification are incorporated herein by references to the same extent as the incorporation of the individual documents, patent applications, and technical standards by references are described specifically and individually.

What is claimed is:

1. A mobile radiography apparatus comprising:
    an irradiator that emits radiation;
    a carriage portion on which the irradiator is mounted and which is capable of traveling;
    steering casters which are provided in the carriage portion and are connected to a steering and whose steering angle is given by an operation of the steering;
    free casters which are provided in the carriage portion and are not connected to the steering and whose steering angle is changed subordinately according to a direction of force applied to the carriage portion; and
    a switching mechanism that selectively switches between a first grounded state in which the free casters are separated from a floor and the steering casters are grounded to the floor and a second grounded state in which the free casters are grounded to the floor and the steering casters are separated from the floor.

2. The mobile radiography apparatus according to claim 1,
    wherein the switching mechanism raises and lowers the free casters with respect to the steering casters to switch between the first grounded state and the second grounded state.

3. The mobile radiography apparatus according to claim 2,
    wherein the switching mechanism has a pedal that raises and lowers the free casters.

4. The mobile radiography apparatus according to claim 1, wherein always-grounded casters that are grounded to the floor in both the first grounded state and the second grounded state are provided, in addition to the free casters and the steering casters.

5. The mobile radiography apparatus according to claim 4,
wherein an arm that supports the irradiator and a main body portion including a controller that controls the irradiator are mounted on the carriage portion,
the always-grounded casters are casters whose steering angle is changed subordinately similarly to the free casters, and
in a case in which a side on which the arm is provided is a front side of the carriage portion and a side on which the main body portion is provided is a rear side of the carriage portion, the always-grounded casters, the steering casters, and the free casters are disposed in this order from the front side to the rear side of the carriage portion.

6. The mobile radiography apparatus according to claim 5,
wherein the steering casters are disposed at a position of a center of gravity in a front-rear direction of the carriage portion.

7. The mobile radiography apparatus according to claim 5,
wherein the arm has two end portions,
the irradiator is provided at one end of the arm, and
an image receiver that receives the radiation, which has been emitted from the irradiator and transmitted through the subject, is provided at the other end of the arm.

8. The mobile radiography apparatus according to claim 1, further comprising:
a steering lock mechanism that locks an operation by the steering in the second grounded state in which the steering casters are separated from the floor.

9. The mobile radiography apparatus according to claim 1,
wherein a handle for pushing and pulling the carriage portion is provided separately from the steering.

* * * * *